(12) United States Patent
Curry et al.

(10) Patent No.: US 8,900,431 B2
(45) Date of Patent: Dec. 2, 2014

(54) ANALYTE SENSOR

(75) Inventors: Kenneth Curry, Oceanside, CA (US); James R. Petisce, San Clemente, CA (US); Henry Oviatt, Temecula, CA (US); Mena Valiket, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/061,487

(22) PCT Filed: Aug. 25, 2009

(86) PCT No.: PCT/US2009/054855
§ 371 (c)(1),
(2), (4) Date: Apr. 11, 2011

(87) PCT Pub. No.: WO2010/027771
PCT Pub. Date: Mar. 11, 2010

(65) Prior Publication Data
US 2011/0186429 A1    Aug. 4, 2011

Related U.S. Application Data

(60) Provisional application No. 61/172,919, filed on Apr. 27, 2009, provisional application No. 61/092,381, filed on Aug. 27, 2008.

(51) Int. Cl.
*G01N 27/327* (2006.01)
*C12Q 1/26* (2006.01)
*C12Q 1/54* (2006.01)

(52) U.S. Cl.
CPC ... *C12Q 1/26* (2013.01); *C12Q 1/54* (2013.01)
USPC ..................................... 204/403.1; 600/347

(58) Field of Classification Search
USPC ............... 204/400, 403.09–403.15; 205/775, 205/777.5; 600/345–348; 435/4–40.52; 422/68.1–98; 436/62–71, 500–548
See application file for complete search history.

(56) References Cited

U.S. PATENT DOCUMENTS 3,512,517 A    5/1970  Kadish
3,539,455 A   11/1970  Clark
(Continued)

FOREIGN PATENT DOCUMENTS

DE   102004056587 A1   5/2006
DE   202006016617 U1   1/2007
(Continued)

OTHER PUBLICATIONS

Lisette B. Verbrugge MD, Deborah Crisis, RN, M Higgins BSce, MBA and Harry B van Wezel MD, PhD, "Accuracy of a Prototype Central Venous Continuous Amperometric Glucose Sensor," American Society of Anesthesiology (ASA) meeting in Oct. 2007.
(Continued)

*Primary Examiner* — Luan Van
*Assistant Examiner* — Gurpreet Kaur
(74) *Attorney, Agent, or Firm* — Michael Crapenhoft

(57) ABSTRACT

Electrochemical sensors for measuring an analyte in a subject are described. More particularly, devices for measurement of an analyte incorporating a sensor comprising a hydrophilic polymer-enzyme composition covering an electroactive surface providing rapid and accurate analyte levels upon deployment are disclosed.

18 Claims, 20 Drawing Sheets

(56) References Cited

U.S. PATENT DOCUMENTS

| | | |
|---|---|---|
| 3,542,662 A | 11/1970 | Hicks |
| 3,837,339 A | 9/1974 | Aisenberg et al. |
| 3,979,274 A | 9/1976 | Newman |
| 4,004,979 A | 1/1977 | Avrameas et al. |
| 4,223,110 A | 9/1980 | Phillips et al. |
| 4,224,125 A | 9/1980 | Nakamura et al. |
| 4,271,278 A | 6/1981 | Phillips et al. |
| 4,314,905 A | 2/1982 | Etzel et al. |
| 4,352,360 A | 10/1982 | King |
| 4,398,346 A | 8/1983 | Underhill et al. |
| 4,430,397 A | 2/1984 | Untereker |
| 4,440,175 A | 4/1984 | Wilkins |
| 4,464,468 A | 8/1984 | Avrameas et al. |
| 4,465,743 A | 8/1984 | Skarstad et al. |
| 4,484,987 A | 11/1984 | Gough |
| 4,514,276 A | 4/1985 | Covington et al. |
| 4,538,616 A | 9/1985 | Rogoff |
| 4,542,291 A | 9/1985 | Zimmerman |
| 4,549,952 A | 10/1985 | Columbus |
| 4,568,335 A | 2/1986 | Updike et al. |
| 4,608,322 A | 8/1986 | Howard et al. |
| 4,621,049 A | 11/1986 | Wang |
| 4,650,547 A | 3/1987 | Gough |
| 4,685,463 A | 8/1987 | Williams |
| 4,705,503 A | 11/1987 | Dorman et al. |
| 4,830,013 A | 5/1989 | Maxwell |
| 4,894,339 A | 1/1990 | Hanazato et al. |
| 4,900,933 A | 2/1990 | Nestor et al. |
| 4,919,770 A | 4/1990 | Preidel et al. |
| 4,933,048 A | 6/1990 | Lauks |
| 4,937,444 A | 6/1990 | Zimmerman |
| 4,952,406 A | 8/1990 | Brown et al. |
| 4,983,524 A | 1/1991 | Fujikawa et al. |
| 4,994,167 A | 2/1991 | Shults et al. |
| 5,034,330 A | 7/1991 | Yamori et al. |
| 5,112,455 A | 5/1992 | Cozzette et al. |
| 5,120,420 A * | 6/1992 | Nankai et al. ............ 204/403.11 |
| 5,165,407 A | 11/1992 | Wilson et al. |
| 5,183,549 A | 2/1993 | Joseph et al. |
| 5,192,415 A | 3/1993 | Yoshioka et al. |
| 5,229,282 A | 7/1993 | Yoshioka et al. |
| 5,262,305 A | 11/1993 | Heller et al. |
| 5,264,103 A | 11/1993 | Yoshioka et al. |
| 5,278,200 A | 1/1994 | Coury et al. |
| 5,284,140 A | 2/1994 | Allen et al. |
| 5,302,444 A | 4/1994 | Jackson et al. |
| 5,312,590 A | 5/1994 | Gunasingham |
| 5,330,527 A | 7/1994 | Montecalvo et al. |
| 5,331,966 A | 7/1994 | Bennett et al. |
| 5,352,348 A | 10/1994 | Young et al. |
| 5,390,671 A | 2/1995 | Lord et al. |
| 5,391,250 A | 2/1995 | Cheney, II et al. |
| 5,397,451 A | 3/1995 | Senda et al. |
| 5,423,883 A | 6/1995 | Helland |
| 5,429,735 A | 7/1995 | Johnson et al. |
| 5,434,017 A | 7/1995 | Berkowitz et al. |
| 5,439,760 A | 8/1995 | Howard et al. |
| 5,455,123 A | 10/1995 | Helgeson et al. |
| 5,455,999 A | 10/1995 | Weiss et al. |
| 5,458,997 A | 10/1995 | Crespi et al. |
| 5,482,473 A | 1/1996 | Lord et al. |
| 5,486,215 A | 1/1996 | Kelm et al. |
| 5,494,562 A | 2/1996 | Maley et al. |
| 5,497,772 A | 3/1996 | Schulman et al. |
| 5,520,788 A | 5/1996 | Johnson |
| 5,538,511 A | 7/1996 | Van Antwerp |
| 5,549,985 A | 8/1996 | Heller et al. |
| 5,568,806 A | 10/1996 | Cheney, II et al. |
| 5,569,186 A | 10/1996 | Lord et al. |
| 5,569,629 A | 10/1996 | TenEyck et al. |
| 5,585,312 A | 12/1996 | TenEyck et al. |
| 5,586,553 A | 12/1996 | Halili et al. |
| 5,607,463 A | 3/1997 | Schwartz et al. |
| 5,607,565 A | 3/1997 | Azarnia et al. |
| 5,660,163 A | 8/1997 | Schulman et al. |
| 5,665,065 A | 9/1997 | Colman et al. |
| 5,696,314 A | 12/1997 | McCaffrey et al. |
| 5,697,899 A | 12/1997 | Hillman et al. |
| 5,704,354 A | 1/1998 | Preidel et al. |
| 5,707,502 A | 1/1998 | McCaffrey et al. |
| 5,728,420 A | 3/1998 | Keogh |
| 5,741,211 A | 4/1998 | Renirie et al. |
| 5,746,899 A | 5/1998 | Finbow et al. |
| 5,766,839 A | 6/1998 | Johnson et al. |
| 5,777,060 A | 7/1998 | Van Antwerp |
| 5,779,665 A | 7/1998 | Mastrototaro et al. |
| 5,786,439 A | 7/1998 | Van Antwerp et al. |
| 5,788,678 A | 8/1998 | Van Antwerp |
| 5,804,048 A | 9/1998 | Wong et al. |
| 5,838,546 A | 11/1998 | Miyoshi |
| 5,852,126 A | 12/1998 | Barnard et al. |
| 5,882,494 A | 3/1999 | Van Antwerp |
| 5,891,506 A | 4/1999 | Keogh |
| 5,899,855 A | 5/1999 | Brown |
| 5,906,916 A | 5/1999 | Wu |
| 5,914,179 A | 6/1999 | Inaba |
| 5,919,216 A | 7/1999 | Houben et al. |
| 5,925,552 A | 7/1999 | Keogh et al. |
| 5,935,886 A | 8/1999 | Jensen et al. |
| 5,945,319 A | 8/1999 | Keogh |
| 5,951,521 A | 9/1999 | Mastrototaro et al. |
| 5,965,380 A | 10/1999 | Heller et al. |
| 5,987,361 A | 11/1999 | Mortimer |
| 5,992,211 A | 11/1999 | Skrtic |
| 5,994,444 A | 11/1999 | Trescony et al. |
| 6,001,067 A | 12/1999 | Shults et al. |
| 6,001,239 A | 12/1999 | Douglas et al. |
| 6,017,741 A | 1/2000 | Keogh |
| 6,033,719 A | 3/2000 | Keogh |
| 6,033,866 A | 3/2000 | Guo et al. |
| 6,038,475 A | 3/2000 | Sikorski et al. |
| 6,071,391 A | 6/2000 | Gotoh et al. |
| 6,093,167 A | 7/2000 | Houben et al. |
| 6,093,172 A | 7/2000 | Funderburk et al. |
| 6,093,506 A | 7/2000 | Crespi et al. |
| 6,101,973 A | 8/2000 | Stewart et al. |
| 6,103,033 A | 8/2000 | Say et al. |
| 6,118,652 A | 9/2000 | Casby et al. |
| 6,124,397 A | 9/2000 | Smith |
| 6,125,291 A | 9/2000 | Miesel et al. |
| 6,129,742 A | 10/2000 | Wu et al. |
| 6,134,459 A | 10/2000 | Roberts et al. |
| 6,134,461 A | 10/2000 | Say et al. |
| 6,135,978 A | 10/2000 | Houben et al. |
| 6,136,735 A | 10/2000 | Gallo et al. |
| 6,139,718 A | 10/2000 | Kurnik et al. |
| D433,755 S | 11/2000 | Mastrototaro et al. |
| 6,143,354 A | 11/2000 | Koulik et al. |
| 6,144,866 A | 11/2000 | Miesel et al. |
| 6,144,871 A | 11/2000 | Saito et al. |
| 6,162,611 A | 12/2000 | Heller et al. |
| 6,163,723 A | 12/2000 | Roberts et al. |
| 6,175,752 B1 | 1/2001 | Say et al. |
| 6,176,988 B1 | 1/2001 | Kessler |
| 6,198,952 B1 | 3/2001 | Miesel |
| 6,200,265 B1 | 3/2001 | Walsh et al. |
| 6,205,358 B1 | 3/2001 | Haeg et al. |
| 6,212,416 B1 | 4/2001 | Ward et al. |
| 6,218,016 B1 | 4/2001 | Tedeschi et al. |
| 6,223,083 B1 | 4/2001 | Rosar |
| 6,248,067 B1 | 6/2001 | Causey, III et al. |
| 6,252,032 B1 | 6/2001 | Van Antwerp et al. |
| 6,254,586 B1 | 7/2001 | Mann et al. |
| 6,261,280 B1 | 7/2001 | Houben et al. |
| 6,274,265 B1 | 8/2001 | Kraska et al. |
| 6,284,478 B1 | 9/2001 | Heller et al. |
| 6,284,550 B1 | 9/2001 | Carroll et al. |
| 6,293,925 B1 | 9/2001 | Safabash et al. |
| 6,295,473 B1 | 9/2001 | Rosar |
| 6,303,179 B1 | 10/2001 | Koulik et al. |
| D452,323 S | 12/2001 | Mastrototaro et al. |
| 6,329,161 B1 | 12/2001 | Heller et al. |
| 6,340,421 B1 | 1/2002 | Vachon et al. |
| 6,360,888 B1 | 3/2002 | McIvor et al. |

(56) References Cited

U.S. PATENT DOCUMENTS

| | | | |
|---|---|---|---|
| 6,368,274 B1 | 4/2002 | Van Antwerp et al. | |
| 6,405,066 B1 | 6/2002 | Essenpreis et al. | |
| 6,413,393 B1 | 7/2002 | Van Antwerp et al. | |
| 6,418,332 B1 | 7/2002 | Mastrototaro et al. | |
| 6,424,847 B1 | 7/2002 | Mastrototaro et al. | |
| 6,438,407 B1 | 8/2002 | Ousdigian et al. | |
| 6,454,710 B1 | 9/2002 | Ballerstadt et al. | |
| 6,456,875 B1 | 9/2002 | Wilkinson et al. | |
| 6,462,162 B2 | 10/2002 | Van Antwerp et al. | |
| 6,471,839 B1 | 10/2002 | Yamamoto et al. | |
| 6,477,395 B2 | 11/2002 | Schulman et al. | |
| 6,484,045 B1 | 11/2002 | Holker et al. | |
| 6,484,046 B1 | 11/2002 | Say et al. | |
| 6,491,803 B1 * | 12/2002 | Shen et al. | 204/403.11 |
| D469,540 S | 1/2003 | Holker et al. | |
| 6,512,939 B1 | 1/2003 | Colvin et al. | |
| 6,520,326 B2 | 2/2003 | McIvor et al. | |
| 6,523,392 B2 | 2/2003 | Porter et al. | |
| 6,558,345 B1 | 5/2003 | Houben et al. | |
| 6,558,351 B1 | 5/2003 | Steil et al. | |
| 6,558,734 B2 | 5/2003 | Koulik et al. | |
| 6,560,471 B1 | 5/2003 | Heller et al. | |
| 6,565,509 B1 | 5/2003 | Plante et al. | |
| 6,572,542 B1 | 6/2003 | Houben et al. | |
| 6,572,748 B1 | 6/2003 | Herrmann et al. | |
| 6,577,899 B2 | 6/2003 | Lebel et al. | |
| 6,579,690 B1 | 6/2003 | Bonnecaze et al. | |
| 6,592,746 B1 | 7/2003 | Schmid-Schoenbein et al. | |
| 6,605,039 B2 | 8/2003 | Houben et al. | |
| 6,617,142 B2 | 9/2003 | Keogh et al. | |
| 6,635,045 B2 | 10/2003 | Carey et al. | |
| 6,641,533 B2 | 11/2003 | Causey, III et al. | |
| 6,642,015 B2 | 11/2003 | Vachon et al. | |
| 6,666,821 B2 | 12/2003 | Keimel | |
| 6,669,663 B1 | 12/2003 | Thompson | |
| 6,671,554 B2 | 12/2003 | Gibson et al. | |
| 6,678,559 B1 | 1/2004 | Breyen et al. | |
| 6,695,958 B1 | 2/2004 | Adam et al. | |
| 6,731,976 B2 | 5/2004 | Penn et al. | |
| 6,740,215 B1 * | 5/2004 | Nakaminami et al. | 204/403.14 |
| 6,784,274 B2 | 8/2004 | Van Antwerp et al. | |
| 6,787,013 B2 | 9/2004 | Chang et al. | |
| 6,809,507 B2 | 10/2004 | Morgan et al. | |
| 6,810,290 B2 | 10/2004 | Lebel et al. | |
| 6,811,533 B2 | 11/2004 | Lebel et al. | |
| 6,811,659 B2 | 11/2004 | Vachon et al. | |
| 6,813,519 B2 | 11/2004 | Lebel et al. | |
| 6,833,612 B2 | 12/2004 | Kinsman | |
| 6,885,107 B2 | 4/2005 | Kinsman | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,895,265 B2 | 5/2005 | Silver | |
| 6,899,813 B2 | 5/2005 | Dolecek et al. | |
| 6,908,535 B2 | 6/2005 | Rankin et al. | |
| 6,915,147 B2 | 7/2005 | Lebel et al. | |
| 6,922,330 B2 | 7/2005 | Nielsen et al. | |
| 6,923,936 B2 | 8/2005 | Swanson et al. | |
| 6,940,141 B2 | 9/2005 | Kinsman | |
| 6,942,518 B2 | 9/2005 | Liamos et al. | |
| 6,956,295 B2 | 10/2005 | Kinsman | |
| 6,960,466 B2 | 11/2005 | Pamidi et al. | |
| 6,964,886 B2 | 11/2005 | Kinsman | |
| 6,966,977 B2 | 11/2005 | Hasegawa et al. | |
| 6,972,423 B2 | 12/2005 | Welland et al. | |
| 6,973,706 B2 | 12/2005 | Say et al. | |
| 6,985,764 B2 | 1/2006 | Mason et al. | |
| 6,990,366 B2 | 1/2006 | Say et al. | |
| 6,991,096 B2 | 1/2006 | Gottlieb et al. | |
| 7,003,336 B2 | 2/2006 | Holker et al. | |
| 7,003,340 B2 | 2/2006 | Say et al. | |
| 7,003,341 B2 | 2/2006 | Say et al. | |
| 7,006,858 B2 | 2/2006 | Silver et al. | |
| 7,018,336 B2 | 3/2006 | Enegren et al. | |
| 7,022,072 B2 | 4/2006 | Fox et al. | |
| 7,029,444 B2 | 4/2006 | Shin et al. | |
| 7,045,054 B1 * | 5/2006 | Buck et al. | 205/778 |
| 7,074,307 B2 | 7/2006 | Simpson et al. | |
| 7,122,390 B2 | 10/2006 | Kinsman | |
| 7,190,988 B2 | 3/2007 | Say et al. | |
| 7,225,535 B2 | 6/2007 | Feldman et al. | |
| 7,250,095 B2 | 7/2007 | Black et al. | |
| 7,267,665 B2 | 9/2007 | Steil et al. | |
| 7,276,029 B2 | 10/2007 | Goode, Jr. et al. | |
| 7,278,983 B2 | 10/2007 | Ireland et al. | |
| 7,279,174 B2 | 10/2007 | Pacetti et al. | |
| 7,310,544 B2 | 12/2007 | Brister et al. | |
| 7,338,639 B2 | 3/2008 | Burke et al. | |
| 7,366,556 B2 | 4/2008 | Brister et al. | |
| 7,379,765 B2 | 5/2008 | Petisce et al. | |
| 7,424,318 B2 | 9/2008 | Brister et al. | |
| 7,452,452 B2 | 11/2008 | Ren et al. | |
| 7,460,898 B2 | 12/2008 | Brister et al. | |
| 7,467,003 B2 | 12/2008 | Brister et al. | |
| 2003/0010097 A1 | 1/2003 | Porter et al. | |
| 2003/0175841 A1 * | 9/2003 | Watanabe et al. | 435/14 |
| 2003/0204146 A1 | 10/2003 | Carlson | |
| 2004/0064086 A1 | 4/2004 | Gottlieb et al. | |
| 2004/0186362 A1 | 9/2004 | Brauker et al. | |
| 2004/0191428 A1 | 9/2004 | Tsuda et al. | |
| 2004/0211666 A1 | 10/2004 | Pamidi et al. | |
| 2004/0224001 A1 | 11/2004 | Pacetti et al. | |
| 2005/0008537 A1 | 1/2005 | Mosoiu et al. | |
| 2005/0033132 A1 | 2/2005 | Shults et al. | |
| 2005/0049313 A1 * | 3/2005 | Nishizawa et al. | 514/682 |
| 2005/0054909 A1 | 3/2005 | Petisce et al. | |
| 2005/0115832 A1 | 6/2005 | Simpson et al. | |
| 2005/0124020 A1 | 6/2005 | Lee et al. | |
| 2005/0154374 A1 | 7/2005 | Hunter et al. | |
| 2005/0233407 A1 | 10/2005 | Pamidi et al. | |
| 2005/0242479 A1 | 11/2005 | Petisce et al. | |
| 2005/0245799 A1 | 11/2005 | Brauker et al. | |
| 2005/0272989 A1 | 12/2005 | Shah et al. | |
| 2006/0003398 A1 | 1/2006 | Heller et al. | |
| 2006/0015020 A1 | 1/2006 | Neale et al. | |
| 2006/0019327 A1 | 1/2006 | Brister et al. | |
| 2006/0020189 A1 | 1/2006 | Brister et al. | |
| 2006/0020191 A1 | 1/2006 | Brister et al. | |
| 2006/0036140 A1 | 2/2006 | Brister et al. | |
| 2006/0036142 A1 | 2/2006 | Brister et al. | |
| 2006/0036143 A1 | 2/2006 | Brister et al. | |
| 2006/0079809 A1 | 4/2006 | Goldberger et al. | |
| 2006/0134716 A1 | 6/2006 | Gouma | |
| 2006/0142651 A1 | 6/2006 | Brister et al. | |
| 2006/0155180 A1 | 7/2006 | Brister et al. | |
| 2006/0183871 A1 | 8/2006 | Ward et al. | |
| 2006/0183984 A1 | 8/2006 | Dobbles et al. | |
| 2006/0183985 A1 | 8/2006 | Brister et al. | |
| 2006/0189856 A1 | 8/2006 | Petisce et al. | |
| 2006/0200019 A1 | 9/2006 | Petisce et al. | |
| 2006/0229512 A1 | 10/2006 | Petisce et al. | |
| 2006/0249381 A1 | 11/2006 | Petisce et al. | |
| 2006/0252027 A1 | 11/2006 | Petisce et al. | |
| 2006/0253012 A1 | 11/2006 | Petisce et al. | |
| 2006/0257995 A1 | 11/2006 | Simpson et al. | |
| 2006/0257996 A1 | 11/2006 | Simpson et al. | |
| 2006/0258929 A1 | 11/2006 | Goode et al. | |
| 2006/0263763 A1 | 11/2006 | Simpson et al. | |
| 2006/0263839 A1 | 11/2006 | Ward et al. | |
| 2006/0282001 A1 | 12/2006 | Noel et al. | |
| 2006/0286660 A1 * | 12/2006 | Yon-Hin | 435/287.1 |
| 2007/0016381 A1 | 1/2007 | Kamath et al. | |
| 2007/0027384 A1 | 2/2007 | Brister et al. | |
| 2007/0027385 A1 | 2/2007 | Brister et al. | |
| 2007/0032717 A1 | 2/2007 | Brister et al. | |
| 2007/0038044 A1 | 2/2007 | Dobbles et al. | |
| 2007/0059196 A1 | 3/2007 | Brister et al. | |
| 2007/0066873 A1 | 3/2007 | Kamath et al. | |
| 2007/0073129 A1 | 3/2007 | Shah et al. | |
| 2007/0083160 A1 | 4/2007 | Hall et al. | |
| 2007/0093704 A1 | 4/2007 | Brister et al. | |
| 2007/0102294 A1 | 5/2007 | Dorisio Deininger et al. | |
| 2007/0105176 A1 | 5/2007 | Ibey et al. | |
| 2007/0108048 A1 | 5/2007 | Wang et al. | |

(56) References Cited

U.S. PATENT DOCUMENTS

| | | | |
|---|---|---|---|
| 2007/0119741 A1 | 5/2007 | Wenger et al. | |
| 2007/0131549 A1 | 6/2007 | Cai et al. | |
| 2007/0149875 A1 | 6/2007 | Ouyang et al. | |
| 2007/0163880 A1 | 7/2007 | Woo et al. | |
| 2007/0170073 A1 | 7/2007 | Wang et al. | |
| 2007/0173708 A9 | 7/2007 | Dobbles et al. | |
| 2007/0173709 A1 | 7/2007 | Petisce et al. | |
| 2007/0173710 A1 | 7/2007 | Petisce et al. | |
| 2007/0173712 A1 | 7/2007 | Shah et al. | |
| 2007/0179371 A1 | 8/2007 | Peyser et al. | |
| 2007/0179385 A1 | 8/2007 | Cho et al. | |
| 2007/0191701 A1 | 8/2007 | Feldman et al. | |
| 2007/0197889 A1 | 8/2007 | Brister et al. | |
| 2007/0197890 A1 | 8/2007 | Boock et al. | |
| 2007/0199818 A1 | 8/2007 | Petyt et al. | |
| 2007/0200254 A1 | 8/2007 | Curry | |
| 2007/0202562 A1* | 8/2007 | Curry | 435/14 |
| 2007/0202672 A1 | 8/2007 | Curry | |
| 2007/0213610 A1 | 9/2007 | Say et al. | |
| 2007/0213611 A1 | 9/2007 | Simpson et al. | |
| 2007/0218097 A1 | 9/2007 | Heller et al. | |
| 2007/0219437 A1 | 9/2007 | Schurman et al. | |
| 2007/0219441 A1* | 9/2007 | Carlin et al. | 600/365 |
| 2007/0227907 A1 | 10/2007 | Shah et al. | |
| 2007/0235331 A1 | 10/2007 | Simpson et al. | |
| 2007/0243566 A1 | 10/2007 | Boenitz-Dulat et al. | |
| 2007/0249916 A1 | 10/2007 | Pesach et al. | |
| 2007/0249920 A1 | 10/2007 | Say et al. | |
| 2007/0264634 A1 | 11/2007 | Bock et al. | |
| 2007/0292896 A1 | 12/2007 | Strano et al. | |
| 2008/0026473 A1* | 1/2008 | Wang et al. | 436/63 |
| 2008/0029390 A1 | 2/2008 | Roche et al. | |
| 2008/0033264 A1 | 2/2008 | Lonneker-Lammers et al. | |
| 2008/0044911 A1 | 2/2008 | Bock et al. | |
| 2008/0071156 A1 | 3/2008 | Brister et al. | |
| 2008/0083617 A1 | 4/2008 | Simpson et al. | |
| 2008/0086042 A1 | 4/2008 | Brister et al. | |
| 2008/0086044 A1 | 4/2008 | Brister et al. | |
| 2008/0086273 A1 | 4/2008 | Shults et al. | |
| 2008/0108942 A1 | 5/2008 | Brister et al. | |
| 2008/0119703 A1 | 5/2008 | Brister et al. | |
| 2008/0119704 A1 | 5/2008 | Brister et al. | |
| 2008/0119706 A1 | 5/2008 | Brister et al. | |
| 2008/0125751 A1 | 5/2008 | Fjield et al. | |
| 2008/0160384 A1 | 7/2008 | Iqbal et al. | |
| 2008/0177166 A1 | 7/2008 | Pronovost et al. | |
| 2008/0188731 A1 | 8/2008 | Brister et al. | |
| 2008/0194935 A1 | 8/2008 | Brister et al. | |
| 2008/0194938 A1 | 8/2008 | Brister et al. | |
| 2008/0197024 A1 | 8/2008 | Simpson et al. | |
| 2008/0200788 A1 | 8/2008 | Brister et al. | |
| 2008/0200789 A1* | 8/2008 | Brister et al. | 600/347 |
| 2008/0200791 A1 | 8/2008 | Simpson et al. | |
| 2008/0214915 A1 | 9/2008 | Brister et al. | |
| 2008/0214918 A1 | 9/2008 | Brister et al. | |
| 2008/0237063 A1 | 10/2008 | Chen | |
| 2008/0242961 A1 | 10/2008 | Brister et al. | |
| 2009/0030294 A1 | 1/2009 | Petisce et al. | |
| 2009/0050477 A1 | 2/2009 | Catt et al. | |
| 2009/0076356 A1 | 3/2009 | Simpson et al. | |
| 2009/0084678 A1 | 4/2009 | Joshi et al. | |
| 2009/0099436 A1 | 4/2009 | Brister et al. | |
| 2009/0236222 A1* | 9/2009 | Murase et al. | 204/403.14 |
| 2009/0240121 A1 | 9/2009 | Bickoff | |

FOREIGN PATENT DOCUMENTS

| | | |
|---|---|---|
| EP | 0351851 A2 | 1/1990 |
| WO | WO-96/11626 A1 | 4/1996 |
| WO | WO-02102224 A2 | 12/2002 |
| WO | WO-2005/074612 A2 | 8/2005 |
| WO | WO-2006/005033 A2 | 1/2006 |
| WO | WO-2007/098187 A2 | 8/2007 |
| WO | WO-2007100588 A1 | 9/2007 |

OTHER PUBLICATIONS

Berger, et al., Structure and Interactions in Covalently and Ionically Crosslinked Chitosan Hydrogels for Biomedical Applications, Europ. J. Pharm. Biopharm., vol. 57, No. 1, pp. 19-34 (2004).

Fiorito et al.; Glucose Amperometric Biosensor Based on the Co-immobilizationi of Glucose Oxidase (GOx) and Ferrocene in Poly(pyrrole) Generated from ethanol/water mixtures; J. Braz. Chem. Soc., vol. 12. No. 6 729-733, 2001.

Garg et al., "Improvement in Glycemic Excursions with a Transcutaneous, Real-Time Continuous Glucose Sensor,"Diabetes Care, (2006) 29: 44-50.

Krajewska; "Application of chitin- and chitosan based materials for enzyme immobilization: a review;" Enzyme Microb Technol 35 (2004), pp. 126-139.

Markey et al., "Immobilization of Catalase and Glucose Oxidase on Inorganic Supports," Biotechnology and Engineering (1975) 17:285.

Miao, et al.; "Amperometric Glucose Biosensor Based on Immobilization of Glucose Oxidase in Chitosan Matrix cross-linked with glutaraldehyde," Electroanalysis (2001) 46:347-49.

Renard, "Implantable Glucose Sensors for Diabetes Monitoring," Minim Invasive Ther Allied Technol, 13:78-86 (2004).

Sternberg, et al., "Study and Development of Multilayer Needle-type Enzyme-based Glucose Microsensors," Biosensors 4: 27-40 (1988).

Urban, et al.; "Minitaurized thin-film biosensors using covalently immobilized glucose oxidase," May 4, 1990; accepted Jan. 23, 1991; Biosensors & Bioelectronics 6 (1991) 555-562.

Updike et al., "The Enzyme Electrode," Nature. vol. 214: 986 (1967).

Wang, "Glucose Biosensors: 40 Years of Advances and Challenges,"Electroanalysis, vol. 13, No. 12, pp. 983-988 (2001).

Mastrototaro, et al., "An electroenzymatic glucose sensor fabricated on a flexible substrate," Sensors and Actuators B, 5: 139-41 (1991).

Sato, et al.: "Development of Single-wall Carbon Nanotubes Modified Screen-printed Electrode Using a Ferrocent-modified Cationic Surfactant for Amperometric Glucose Biosensor Applications," Sensors and Actuators B, vol. 129, No. 1 pp. 188-194, Jan. 17, 2008.

Xie,J. et al.: "Platinum Decorated Carbon Nanotubes for Highly Sensitive Amperometric Glucose Sensing," Nanotechnology Feb. 14, 2007 Institute of Physics Publishing, vol. 18, No. 8, Feb. 14, 2007.

International Search Report, Feb. 23, 2007, PCT/US2007/004828.

International Search Report, Feb. 17, 2010, PCT/US2009/054855.

Chinese Office Action, Apr. 26, 2010, U.S. Appl. No. 11/710,329.

Chinese Office Action, Mar. 9, 2011, U.S. Appl. No. 11/710,329.

Supplementary European Search Report, Mar. 4, 2014.

* cited by examiner

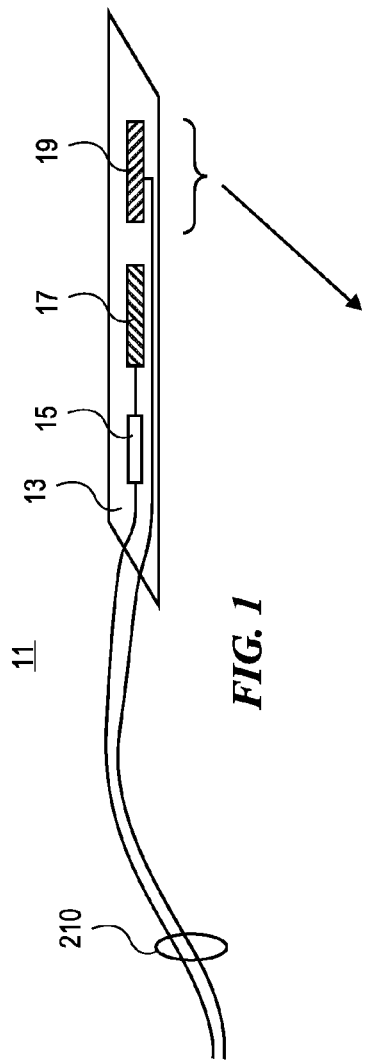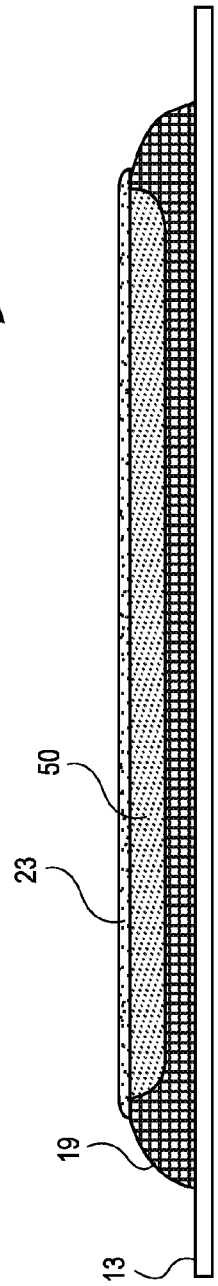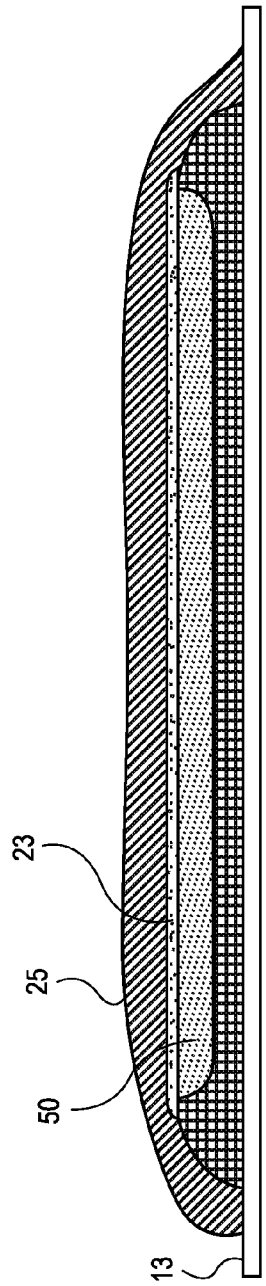

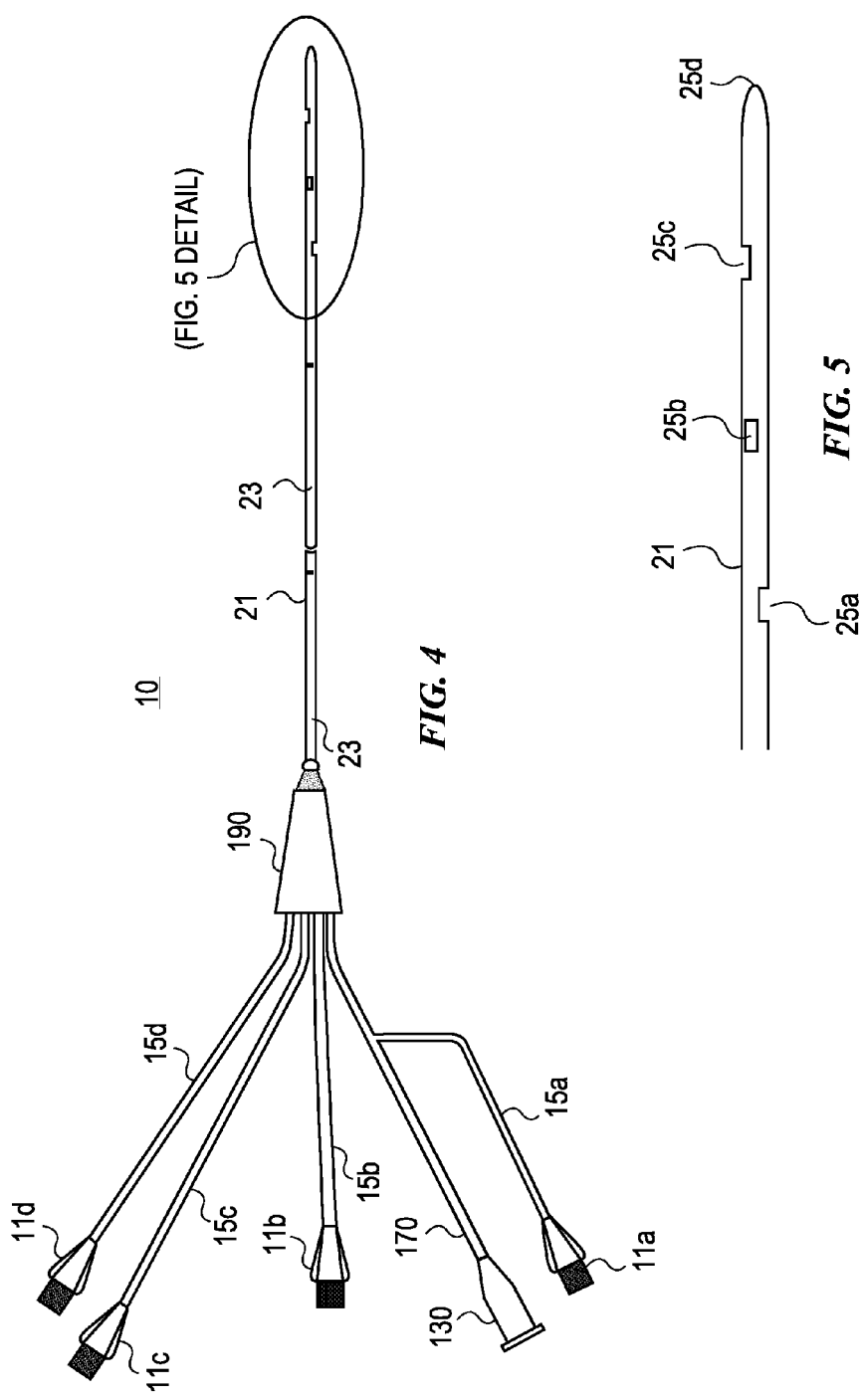

FIG. 21
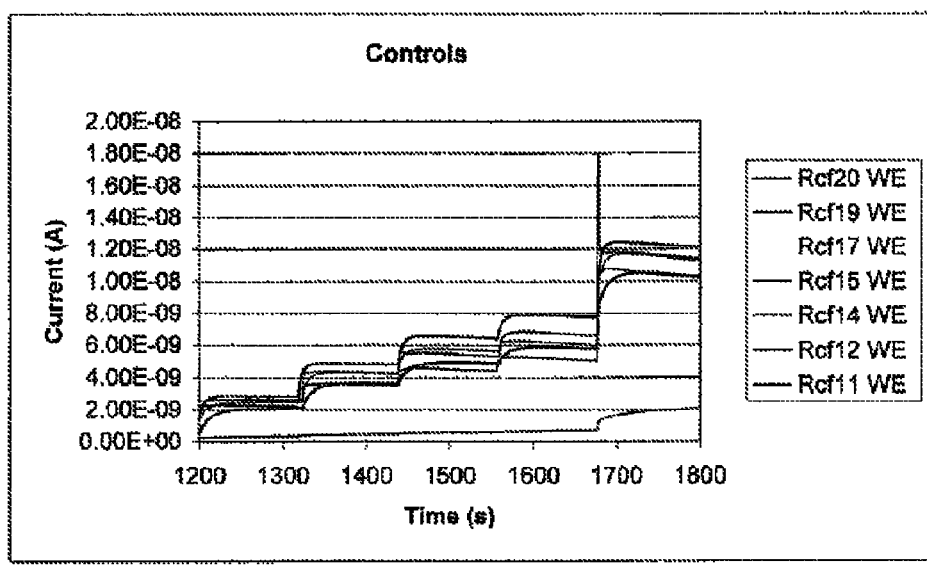
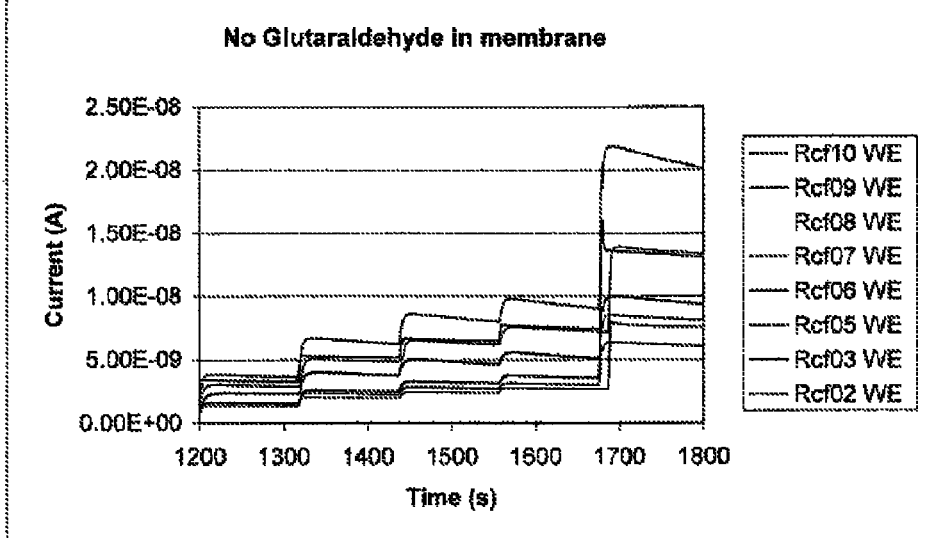

ANALYTE SENSOR

TECHNICAL FIELD

The present disclosure relates generally to devices for measuring an analyte in a subject. More particularly, the present disclosure relates to devices for measurement of an analyte that incorporates a sensor comprising a hydrophilic polymer-enzyme composition in contact with an interference layer for providing rapid and accurate analyte levels upon deployment.

BACKGROUND

Among many problems impeding the development of a practical rapid and accurate amperometric sensor is a current need for the sensor technology to "break-in" or otherwise rapidly reach chemical, electrical and physical equilibrium with its environment and provide a signal that is an accurately representative of the true analyte level. Attempts to reduce break-in in amperometric sensors have been addressed in a number of ways, for example by using separate and distinct hydrophilic layers in a multi-membrane-based system or by incorporating an aqueous reservoir or environment about the sensor, albeit with limited success, because the break-in improvements to date for these systems have generally only provided limited improvements in break-in. In certain cases, such as an intensive care units (ICUs) setting or for continuous glucose monitoring (CGM) applications, break-in requirements would ideally be a few minutes or seconds. Thus, the current amperometric sensors available on the market may not be capable of achieving the required rapid break-in performance needed for specific applications, such as ICU monitoring of analyte levels in a subject.

In certain medical applications, patients in ICU or other emergency situations may be often fitted with invasive appliances such as catheters so that vital fluids or medicine may be administered intravenously. A physician determining a fluid dosage to be provided to a patient intravenously may need to know symptoms as quickly as possible that may only be determined through blood tests. Just how quickly the information is needed depends on the gravity of the situation. In some cases, the speed with which a physiological parameter may be determined may be the difference between life and death. In those situations, the practice of drawing a blood sample and sending it off for laboratory analysis may be entirely too slow.

A more timely method for measuring blood chemistry to ascertain a physiological parameter of interest may eventually be perfected. Thus, there exists an unmet need to provide intravenous amperometric sensing, in which the concentration of an analyte present in a patient's bloodstream may be determined by locating, within the circulatory system, sensor comprising an enzyme electrode that produces a rapid and accurate electrical current proportional to the true analyte concentration, for example, in less than 30 minutes.

SUMMARY

In general, electrochemical analyte sensors and sensor assemblies are disclosed that provide rapid chemical, electrical and physical equilibrium with their environment and as a result, provide fast and accurate analyte levels. Such sensors are of particular use in more demanding sensing applications, such as ICU monitoring.

It is generally known that in some circumstances, an interference layer may alter or reduce the sensitivity of some glucose oxidase-based sensor assemblies and/or require a period of time before constant signal output is achieved. Accordingly, in some circumstances, it is generally believed that a separate "hydrophilic domain" or an "electrolyte phase" should be employed between the electroactive surface (s) (e.g., working and/or reference electrodes) and the interference layer. Alternatively, in some circumstances, it is generally believed that a hydrophilic domain or an electrolyte phase should be employed between the enzyme layer and the interference layer. However, the Applicants have surprisingly observed that the embodiments disclosed herein substantially eliminate or reduce the need for employing a separate intervening hydrophilic domain or a separate intervening electrolyte phase between the electroactive surface and the interference layer, while still achieving rapid and accurate constant signal output. In addition, the Applicants have surprisingly observed that the embodiments disclosed herein substantially eliminate or reduce the need for employing a separate intervening hydrophilic domain or a separate intervening electrolyte phase between the enzyme layer and the interference layer, while achieving rapid constant signal output from the disclosed sensor. Furthermore, and contrary to the accepted wisdom of crosslinking the enzyme in the enzyme layer, Applicants have unexpectedly observed that by preparing the enzyme layer substantially free of a cross-linking agent provides for a sensor having a signal output substantially equivalent to or slightly more than a sensor having a crossed-linked enzyme layer. Furthermore, Applicants have unexpectedly observed that by preparing the enzyme layer substantially free of a cross-linking agent provides for a sensor achieving a rapid constant signal output substantially equivalent to a sensor having a crossed-linked enzyme layer.

In one aspect, an electrochemical analyte sensor is provided. The sensor comprises at least one electroactive surface, an optional interference layer comprising a cellulosic derivative in contact with at least a portion of the electroactive surface, and an enzyme layer comprising a hydrophilic polymer-enzyme composition, at least a portion of the enzyme layer at least partially covering the electroactive surface. The sensor break-in is about 30 minutes or less immediately following deployment.

In one aspect, the sensor is configured without a separate intervening hydrophilic layer or a separate electrolyte layer between the electroactive surface and the interference layer.

In one aspect, the sensor is configured without a separate intervening hydrophilic layer or a separate electrolyte layer between the interference layer and the enzyme layer.

In one aspect, the sensor is configured without a separate intervening hydrophilic layer or a separate electrolyte layer between the electroactive surface and the interference layer and without a separate intervening hydrophilic layer or a separate electrolyte layer between the interference layer and the enzyme layer.

In one aspect, the sensor is configured such that the enzyme layer is substantially free of a cross-linking agent or of the reaction products of a cross-linking agent and the hydrophilic polymer-enzyme composition.

In another aspect, an electrochemical analyte sensor assembly is provided. The assembly comprises a flex circuit comprising at least one reference electrode and at least one working electrode, at least one working electrode having an electroactive surface capable of providing a detectable electrical output upon interaction with an electrochemically detectable species. An optional interference layer at least partially covers a portion of the electroactive surface. An enzyme layer comprising a hydrophilic polymer-enzyme having at least a portion thereof at least partially covering the electroactive surface. Optionally, a membrane covers the hydrophilic polymeric layer, the interference layer and at least a portion of the electroactive surface. The flex circuit is electrically configurable to a control unit capable of at least receiving the detectable electrical output. In other embodiments, the enzyme layer is substantially free of a cross-linking agent or of the reaction products of a cross-linking agent and the hydrophilic polymer-enzyme composition.

In another aspect, a method of intravenously measuring an analyte in a subject is provided. The method comprises providing a catheter comprising the sensor assembly as described herein, introducing the catheter into the vascular system of a subject, and measuring an analyte.

BRIEF DESCRIPTION OF THE DRAWINGS

FIG. 1 shows an amperometric sensor in the form of a flex circuit having a working electrode coated with a flux limiting membrane according to an embodiment of the invention.

FIG. 2 is a side cross-sectional view of a working electrode portion of the sensor of shown prior to application of a flux limiting membrane according to an embodiment of the invention.

FIG. 3 is a cross-sectional view of the working electrode portion of the sensor as in FIG. 2, shown after application of the flux limiting membrane according to an embodiment of the invention.

FIG. 4 is a side view of a multilumen catheter with a sensor assembly according to an embodiment of the invention.

FIG. 5 is a detail of the distal end of the multilumen catheter of FIG. 4 according to an embodiment of the invention.

FIGS. 21A and 21B are graphs depicting current output over time for a sensor embodiment of the present invention comprising an enzyme layer substantially free of a cross-linking agent versus control.

DETAILED DESCRIPTION

Figure 6:
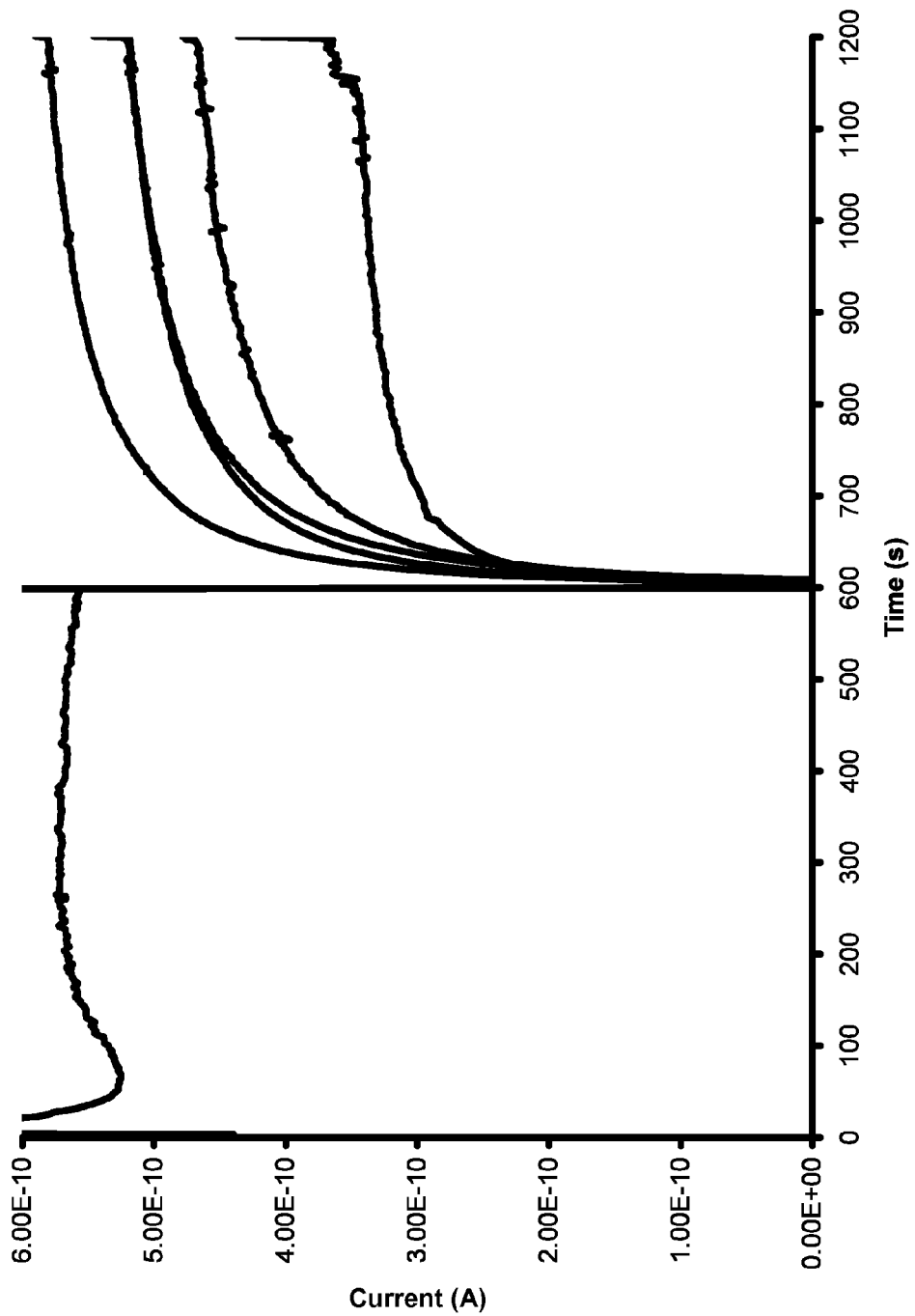
FIG. 6 is a graph of current output verses time for sensor controls during a first use.

Electrochemical analyte sensors for measuring an analyte in a subject are described. More particularly, devices and methods for measurement of an analyte incorporating a sensor comprising a hydrophilic polymer-enzyme composition covering an electroactive surface providing rapid and accurate analyte levels upon deployment are disclosed. The various embodiments disclosed herein describe analyte sensors that substantially eliminate or reduce the need for employing a separate intervening hydrophilic domain or a separate intervening electrolyte phase between the electroactive surface and the interference layer, while still achieving rapid and accurate constant signal output. In addition, the embodiments disclosed herein describe analyte sensors that substantially eliminate or reduce the need for employing a separate intervening hydrophilic domain or a separate intervening electrolyte phase between the enzyme layer and the interference layer, while achieving rapid constant signal output from the disclosed sensor. Furthermore, analyte sensors are described comprising an enzyme layer substantially free of a cross-linking agent, providing sensors having a signal output substantially equivalent to or slightly more than a sensor having a crossed-linked enzyme layer and/or sensors achieving a rapid constant signal output substantially equivalent to a sensor having a crossed-linked enzyme layer.

The following description and examples illustrate some exemplary embodiments of the disclosed invention in detail. Those of skill in the art will recognize that there may be numerous variations and modifications of this invention that may be encompassed by its scope. Accordingly, the description of a certain exemplary embodiment is not intended to limit the scope of the present invention.

DEFINITIONS

In order to facilitate an understanding of the various aspects of the invention, the following are defined below.

The term "analyte" as used herein refers without limitation to a substance or chemical constituent of interest in a biological fluid (for example, blood) that may be analyzed. The analyte may be naturally present in the biological fluid, the analyte may be introduced into the body, or the analyte may be a metabolic product of a substance of interest or an enzymatically produced chemical reactant or chemical product of a substance of interest. Preferably, analytes include chemical entities capable of reacting with at least one enzyme and quantitatively yielding an electrochemically reactive product that is either amperometrically or voltammetrically detectable.

The phrases and terms "analyte measuring device," "sensor," and "sensor assembly" as used herein refer without limitation to an area of an analyte-monitoring device that enables the detection of at least one analyte. For example, the sensor may comprise a non-conductive portion, at least one working electrode, a reference electrode, and a counter electrode (optional), forming an electrochemically reactive surface at one location on the non-conductive portion and an electronic connection at another location on the non-conductive portion, and one or more layers over the electrochemically reactive surface.

The phrase "capable of" as used herein, when referring to recitation of function associated with a recited structure, is inclusive of all conditions where the recited structure can actually perform the recited function. For example, the phrase "capable of" includes performance of the function under normal operating conditions, experimental conditions or laboratory conditions, as well as conditions that may not or cannot occur during normal operation.

The term "cellulose acetate butyrate" as used herein refers without limitation to compounds obtained by contacting cellulose with acetic anhydride and butyric anhydride.

The term "comprising" and its grammatical equivalents, as used herein is synonymous with "including," "containing," or "characterized by," and is inclusive or open-ended and does not exclude additional, unrecited elements or method steps.

The phrases "continuous analyte sensing" and "continual analyte sensing" (and the grammatical equivalents "continuously" and "continually") as used herein refer without limitation to a period of analyte concentration monitoring that is continuously, continually, and/or intermittently (but regularly) performed.

The phrase "continuous glucose sensing" as used herein refers without limitation to a period of glucose concentration monitoring that is continuously, continually, and/or intermittently (but regularly) performed. The period may, for example, at time intervals ranging from fractions of a second up to, for example, 1, 2, or 5 minutes, or longer.

The terms "crosslink" and "crosslinking" as used herein refer without limitation to joining (e.g., adjacent chains of a polymer and/or protein) by creating covalent or ionic bonds. Crosslinking may be accomplished by known techniques, for example, thermal reaction, chemical reaction or ionizing radiation (for example, electron beam radiation, UV radiation, X-ray, or gamma radiation). For example, reaction of a dialdehyde such as glutaraldehyde with a hydrophilic polymer-enzyme composition would result in chemical crosslinking of the enzyme and/or hydrophilic polymer (e.g., the formation of reaction products of the cross-linking agent and the enzyme and/or hydrophilic polymer).

The term "cover" and its grammatical equivalents used herein refer without limitation to its normal dictionary definition, and is inclusive of one or more intervening layers. For example, a layer "covering" at least a portion of an electroactive surface is inclusive of one or more intervening layers between the layer and the electroactive surface.

The phrase "hydrophilic polymer-enzyme composition" refers without limitation to a physical or chemical mixture, a physical blend, a continuous or discontinuous phase, a micelle or a dispersion of at least one enzyme and at least one hydrophilic polymer. The hydrophilic polymer-enzyme composition may further include at least one protein, or a natural or synthetic material.

The term "break-in" as used herein refers without limitation to a time duration, after sensor deployment, where an electrical output from the sensor achieves a substantially constant value following contact of the sensor with a solution. Break-in is inclusive of configuring the sensor electronics by applying different voltage settings, starting with a higher voltage setting and then reducing the voltage setting and/or pre-treating the operating electrode with a negative electric current at a constant current density. Break-in is inclusive of chemical/electrical equilibrium of one or more of the sensor components such as membranes, layers, enzymes and electronics, and may occur prior to calibration of the sensor output. For example, following a potential input to the sensor, an immediate break-in would be a substantially constant current output from the sensor. By way of example, an immediate break-in for a glucose electrochemical sensor after contact with a solution, would be a current output representative of +/−5 mg/dL of a calibrated glucose concentration within about thirty minutes or less after deployment. The term "break-in" is well documented and is appreciated by one skilled in the art of electrochemical glucose sensors, however it may be exemplified for a glucose sensor, as the time at which reference glucose data (e.g., from a Self Monitoring Blood Glucose (SMBG) meter) is within +/−5 mg/dL of the measured glucose sensor data.

The phrase "electroactive surface" as used herein refers without limitation to a surface of an electrode where an electrochemical reaction takes place. For example, at a predetermined potential, $H_2O_2$ reacts with the electroactive surface of a working electrode to produce two protons ($2H^+$), two electrons ($2e^-$) and one molecule of oxygen ($O_2$), for which the electrons produce a detectable electronic current. The electroactive surface may include on at least a portion thereof, a chemically or covalently bonded adhesion promoting agent, such as aminoalkylsilane, and the like.

The term "subject" as used herein refers without limitation to mammals, particularly humans and domesticated animals.

The terms "interferants," "interferents" and "interfering species," as used herein refer without limitation to effects and/or species that otherwise interfere with a measurement of an analyte of interest in a sensor to produce a signal that does not accurately represent the analyte measurement. For example, in an electrochemical sensor, interfering species may be compounds with oxidation potentials that substantially overlap the oxidation potential of the analyte to be measured.

The phrase "enzyme layer" as used herein refers without limitation to a permeable or semi-permeable membrane comprising one or more domains that may be permeable to reactants and/or co-reactants employed in determining the analyte of interest. As an example, an enzyme layer comprises an immobilized glucose oxidase enzyme in a hydrophilic polymer, which catalyzes an electrochemical reaction with glucose and oxygen to permit measurement of a concentration of glucose.

The term "flux limiting membrane" as used herein refers to a semipermeable membrane that controls the flux of oxygen and other analytes to the underlying enzyme layer. By way of example, for a glucose sensor, the flux limiting membrane preferably renders oxygen in a non-rate-limiting excess. As a result, the upper limit of linearity of glucose measurement is extended to a much higher value than that which is achieved without the flux limiting membrane.

The phrase "vinyl ester monomeric units" as used herein refers to compounds and compositions of matter which are formed from the polymerization of an unsaturated monomer having ester functionality. For example, polyethylene vinyl acetate polymer and copolymers thereof are compounds comprising vinyl ester monomeric units.

As used herein, the phrases "substantially absent" and "substantially free" mean at minimum, no amount of material will be deliberately added. Preferably, the amount of material present will be below detectable amounts or be present in trace amounts. More preferably, no amount of material will be present. For example, a sensor according to the present invention that is substantially absent a separate intervening hydrophilic layer between the electroactive surface and the interference layer will preferably be absent any intervening materials or layers between the electrode surface and the interference layer. Further, by way of example, an enzyme layer of the present invention that is "substantially free" of a cross-linking agent is either completely absent of cross-linking agent or its reaction products, or the enzyme layer comprises an amount of cross-linking agent resulting in insignificant cross-linking of the enzyme layer or of insufficient amounts of reaction products of the cross-linking agent with the enzyme or polymer Sensor System and Sensor Assembly The aspects of the invention herein disclosed relate to the use of an analyte sensor system that measures a concentration of analyte of interest or a substance indicative of the concentration or presence of the analyte. The sensor system is a continuous device, and may be used, for example, as or part of a subcutaneous, transdermal (e.g., transcutaneous), or intravascular device. The analyte sensor may use an enzymatic, chemical, electrochemical, or combination of such methods for analyte-sensing. The output signal is typically a raw signal that is used to provide a useful value of the analyte of interest to a user, such as a patient or physician, who may be using the device. Accordingly, appropriate smoothing, calibration, and evaluation methods may be applied to the raw signal.

Generally, the sensor comprises at least a portion of the exposed electroactive surface of a working electrode surrounded by a plurality of layers. In one aspect, an interference layer is deposited over and in contact with at least a portion of the electroactive surface(s) of the sensor (working electrode(s) and optionally the reference electrode) to provide protection of the exposed electrode surface from the biological environment and/or limit or block interferents. An enzyme layer is deposited over and in contact with at least a portion of the interference layer. In one aspect, the interference layer and enzyme layer provides for rapid response and stabilization of the signal output of the sensor and/or eliminates the need to pre-treat the electroactive surface of the electrode with fugitive species, such as salts and electrolyte layers or domains, which simplifies manufacture and reduces lot-to-lot variability of the disclosed sensors. In another aspect, an interference layer, per se, is not used, and the enzyme layer covers at least a portion of the electroactive surfaces of the working electrode with optional additional layers covering at least a portion of the enzyme layer. In this aspect, a blank electrode may be used such that the signal produced from non-analyte interferents may be taken into account.

One exemplary embodiment described in detail below utilizes a medical device, such as a catheter, with a glucose sensor assembly. In one aspect, a medical device with an analyte sensor assembly is provided for inserting the catheter into a subject's vascular system. The medical device with the analyte sensor assembly may include associated therewith an electronics unit associated with the sensor, and a receiver for receiving and/or processing sensor data. Although a few exemplary embodiments of continuous glucose sensors may be illustrated and described herein, it should be understood that the disclosed embodiments may be applicable to any device capable of substantially continual or substantially continuous measurement of a concentration of analyte of interest and for providing a rapid and accurate output signal that is representative of the concentration of that analyte.

Electrode and Electroactive Surface

The electrode and/or the electroactive surface of the sensor or sensor assembly disclosed herein comprises a conductive material, such as platinum, platinum-iridium, palladium, graphite, gold, carbon, conductive polymer, alloys, ink or the like. Although the electrodes can be formed by a variety of manufacturing techniques (bulk metal processing, deposition of metal onto a substrate, or the like), it may be advantageous to form the electrodes from screen printing techniques using conductive and/or catalyzed inks. The conductive inks may be catalyzed with noble metals such as platinum and/or palladium.

In one aspect, the electrodes and/or the electroactive surfaces of the sensor or sensor assembly are formed on a flexible substrate, such as a flex circuit. In one aspect, a flex circuit is part of the sensor and comprises a substrate, conductive traces, and electrodes. The traces and electrodes may be masked and imaged onto the substrate, for example, using screen printing or ink deposition techniques. The traces and the electrodes, and the electroactive surface of the electrodes may be comprised of a conductive material, such as platinum, platinum-iridium, palladium, graphite, gold, carbon, conductive polymer, alloys, ink or the like.

In one aspect, a counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction: Glucose+$O_2$→Gluconate+$H_2O_2$. Oxidation of $H_2O_2$ by the working electrode is balanced by reduction of any oxygen present, or other reducible species at the counter electrode. The $H_2O_2$ produced from the glucose oxidase reaction reacts at the surface of working electrode and produces two protons ($2H^+$), two electrons ($2e^-$), and one oxygen molecule ($O_2$).

In one aspect, additional electrodes may be included within the sensor or sensor assembly, for example, a three-electrode system (working, reference, and counter electrodes) and/or one or more additional working electrodes configured as a baseline subtracting electrode, or which is configured for measuring additional analytes. The two working electrodes may be positioned in close proximity to each other, and in close proximity to the reference electrode. For example, a multiple electrode system may be configured wherein a first working electrode is configured to measure a first signal comprising glucose and baseline and an additional working electrode substantially similar to the first working electrode without an enzyme disposed thereon is configured to measure a baseline signal consisting of baseline only. In this way, the baseline signal generated by the additional electrode may be subtracted from the signal of the first working electrode to produce a glucose-only signal substantially free of baseline fluctuations and/or electrochemically active interfering species.

In one aspect, the sensor comprises from 2 to 4 electrodes. The electrodes may include, for example, the counter electrode (CE), working electrode (WE1), reference electrode (RE) and optionally a second working electrode (WE2). In one aspect, the sensor will have at least a CE, RE and WE1. In one aspect, the addition of a WE2 is used, which may further improve the accuracy of the sensor measurement. In one aspect, the addition of a second counter electrode (CE2) may be used, which may further improve the accuracy of the sensor measurement.

The electroactive surface may be treated prior to application of any of the subsequent layers. Surface treatments may include for example, chemical, plasma or laser treatment of at least a portion of the electroactive surface. By way of example, the electrodes may be chemically or covalently contacted with one or more adhesion promoting agents. Adhesion promoting agents may include for example, aminoalkylalkoxylsilanes, epoxyalkylalkoxylsilanes and the like. For example, one or more of the electrodes may be chemically or covalently contacted with a solution containing 3-glycidoxypropyltrimethoxysilane.

In some alternative embodiments, the exposed surface area of the working (and/or other) electrode may be increased by altering the cross-section of the electrode itself. Increasing the surface area of the working electrode may be advantageous in providing an increased signal responsive to the analyte concentration, which in turn may be helpful in improving the signal-to-noise ratio, for example. The cross-section of the working electrode may be defined by any regular or irregular, circular or non-circular configuration.

Interference Layer

Interferants may be molecules or other species that may be reduced or oxidized at the electrochemically reactive surfaces of the sensor, either directly or via an electron transfer agent, to produce a false positive analyte signal (e.g., a non-analyte-related signal). This false positive signal generally causes the subject's analyte concentration to appear higher than the true analyte concentration. For example, in a hypoglycemic situation, where the subject has ingested an interferant (e.g., acetaminophen), the artificially high glucose signal may lead the subject or health care provider to believe that they are euglycemic or, in some cases, hyperglycemic. As a result, the subject or health care provider may make inappropriate or incorrect treatment decisions.

In one aspect, an interference layer is provided on the sensor or sensor assembly that substantially restricts or eliminates the passage of one or more interfering species. Interfering species for a glucose sensor include, for example, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, urea and uric acid. The interference layer may be less permeable to one or more of the interfering species than to a target analyte species.

In an embodiment, the interference layer is formed from one or more cellulosic derivatives. In one aspect, mixed ester cellulosic derivatives may be used, for example, cellulose acetate butyrate, cellulose acetate phthalate, cellulose acetate propionate, cellulose acetate trimellitate, as well as their copolymers and terpolymers, with other cellulosic or non-cellulosic monomers, including cross-linked variations of the above. Other polymers, such as polymeric polysaccharides having similar properties to cellulosic derivatives, may be used as an interference material or in combination with the above cellulosic derivatives. Other esters of cellulose may be blended with the mixed ester cellulosic derivatives.

In one aspect, the interference layer is formed from cellulose acetate butyrate. Cellulose acetate butyrate is a cellulosic polymer having both acetyl and butyl groups, and hydroxyl groups. A cellulose acetate butyrate having about 35% or less acetyl groups, about 10% to about 25% butyryl groups, and hydroxyl groups making up the remainder may be used. A cellulose acetate butyrate having from about 25% to about 34% acetyl groups and from about 15 to about 20% butyryl groups may also be used, however, other amounts of acetyl and butyryl groups may be used. A preferred cellulose acetate butyrate contains from about 28% to about 30% acetyl groups and from about 16 to about 18% butyryl groups.

Cellulose acetate butyrate with a molecular weight of about 10,000 daltons to about 75,000 daltons is preferred, preferably from about 15,000, 20,000, or 25,000 daltons to about 50,000, 55,000, 60,000, 65,000, or 70,000 daltons, and more preferably about 65,000 daltons is employed. In certain embodiments, however, higher or lower molecular weights may be used or a blend of two or more cellulose acetate butyrates having different molecular weights may be used.

A plurality of layers of cellulose acetate butyrate may be combined to form the interference layer in some embodiments, for example, two or more layers may be employed. It may be desirable to employ a mixture of cellulose acetate butyrates with different molecular weights in a single solution, or to deposit multiple layers of cellulose acetate butyrate from different solutions comprising cellulose acetate butyrate of different molecular weights, different concentrations, and/or different chemistries (e.g., wt % functional groups). Additional substances in the casting solutions or dispersions may be used, e.g., casting aids, defoamers, surface tension modifiers, functionalizing agents, crosslinking agents, other polymeric substances, substances capable of modifying the hydrophilicity/hydrophobicity of the resulting layer, and the like.

The interference material may be sprayed, cast, coated, or dipped directly to the electroactive surface(s) of the sensor. The dispensing of the interference material may be performed using any known thinfilm technique. Two, three or more layers of interference material may be formed by the sequential application and curing and/or drying of the casting solution.

The concentration of solids in the casting solution may be adjusted to deposit a sufficient amount of solids or film on the electrode in one layer (e.g., in one dip or spray) to form a layer sufficient to block an interferant with an oxidation or reduction potential otherwise overlapping that of a measured species (e.g., $H_2O_2$), measured by the sensor. For example, the casting solution's percentage of solids may be adjusted such that only a single layer is required to deposit a sufficient amount to form a functional interference layer that substantially prevents or reduces the equivalent glucose signal of the interferant measured by the sensor. A sufficient amount of interference material would be an amount that substantially prevents or reduces the equivalent glucose signal of the interferant of less than about 30, 20 or 10 mg/dl. By way of example, the interference layer is preferably configured to substantially block about 30 mg/dl of an equivalent glucose signal response that otherwise would be produced by acetaminophen by a sensor without an interference layer. Such equivalent glucose signal response produced by acetaminophen would include a therapeutic dose of acetaminophen. Any number of coatings or layers formed in any order may be suitable for forming the interference layer of the embodiments disclosed herein.

In one aspect, the interference layer is deposited either directly onto the electroactive surfaces of the sensor or onto a material or layer in direct contact with the surface of the electrode. Preferably, the interference layer is deposited directly onto the electroactive surfaces of the sensor substantially without an intervening material or layer in direct contact with the surface of the electrode. It has been surprisingly found that configurations comprising the interference layer deposited directly onto the electroactive surface of the sensor substantially eliminates the need for an intervening layer between the electroactive surface and the interference layer while still providing a rapid and accurate signal representative of the analyte.

The interference layer may be applied to provide a thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes may also be desirable in certain embodiments, but thinner membranes may be generally preferred because they generally have a lower affect on the rate of diffusion of hydrogen peroxide from the enzyme membrane to the electrodes.

Enzyme Layer

The sensor or sensor assembly disclosed herein includes an enzyme layer. The enzyme layer may be formed of a hydrophilic polymer-enzyme composition. It has been surprisingly found that the configuration where the enzyme layer is deposited directly onto at least a portion of the interference layer or directly onto at least a portion of the electroactive surface may substantially eliminate the need for an intervening layer between the interference layer or the enzyme layer while still providing a rapid and accurate signal representative of the analyte. In one aspect, the enzyme layer comprises an enzyme deposited directly onto at least a portion of the interference layer. In one aspect, the enzyme layer comprises a hydrophilic polymer-enzyme composition deposited directly onto at least a portion of the electroactive surface.

In one aspect, the enzyme layer comprises an enzyme and a hydrophilic polymer selected from poly-N-vinylpyrrolidone (PVP), poly-N-vinyl-3-ethyl-2-pyrrolidone, poly-N-vinyl-4,5-dimethyl-2-pyrrolidone, polyacrylamide, poly-N,N-dimethylacrylamide, polyurethane, polyvinyl alcohol, polymers with pendent ionizable groups and copolymers thereof. Preferably, the enzyme layer comprises poly-N-vinylpyrrolidone. In other embodiments, the enzyme layer may comprise glucose oxidase, poly-N-vinylpyrrolidone and an amount of crosslinking agent sufficient to immobilize the enzyme.

The molecular weight of the hydrophilic polymer of the enzyme layer is such that fugitive species are prevented or substantially inhibited from leaving the sensor environment and more particularly, fugitive species are prevented or substantially inhibited from leaving the enzyme's environment when the sensor is initially deployed.

The hydrophilic polymer-enzyme composition of the enzyme layer may further include at least one protein and/or natural or synthetic material. For example, the hydrophilic polymer-enzyme composition of the enzyme layer may further include, for example, serum albumins, polyallylamines, polyamines and the like, as well as combination thereof.

The enzyme is preferably immobilized in the sensor. The enzyme may be encapsulated within the hydrophilic polymer and may be cross-linked or otherwise immobilized therein. Thus, the enzyme may be immobilized without cross-linking or producing cross-linking reaction products, as described below. The enzyme may be cross-linked or otherwise immobilized optionally together with at least one protein and/or natural or synthetic material. In one aspect, the hydrophilic polymer-enzyme composition comprises glucose oxidase, bovine serum albumin, and poly-N-vinylpyrrolidone. The composition may further include a cross-linking agent, for example, a dialdehyde such as glutaraldehdye, to cross-link or otherwise immobilize the components of the composition.

In one aspect, other proteins and/or natural or synthetic materials may be substantially excluded from the hydrophilic polymer-enzyme composition of the enzyme layer. For example, the hydrophilic polymer-enzyme composition may be substantially free of bovine serum albumin Bovine albumin-free compositions may be desirable for meeting various governmental regulatory requirements. Thus, in one aspect, the enzyme layer comprises glucose oxidase and a sufficient amount of cross-linking agent, for example, a dialdehyde such as glutaraldehyde, to cross-link or otherwise immobilize the enzyme. In another aspect, the enzyme layer comprises glucose oxidase, poly-N-vinylpyrrolidone and a sufficient amount of cross-linking agent to cross-link or otherwise immobilize the enzyme.

In another aspect, the enzyme layer is substantially free of a cross-linking agent or the reaction products of a cross-linking agent and the hydrophilic polymer-enzyme composition. For example, the hydrophilic polymer-enzyme composition is substantially free of a dialdehyde cross-linking agent such as glutaraldehyde or contact therewith. Thus, in one aspect, the enzyme layer comprises glucose oxidase and a hydrophilic polymer, such as poly-N-vinylpyrrolidone, and is substantially free of a cross-linking agent or the reaction products of a cross-linking agent and the glucose oxidase or poly-N-vinylpyrrolidone.

In another aspect, the enzyme layer comprises glucose oxidase, a hydrophilic polymer, such as poly-N-vinylpyrrolidone, and/or at least one protein and/or natural or synthetic material, such as bovine serum albumen, the enzyme layer being substantially free of a cross-linking agent or the reaction products of a cross-linking agent and the glucose oxidase, the poly-N-vinylpyrrolidone, or the at least one protein and/or natural or synthetic material.

The enzyme layer thickness may be from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. Preferably, the enzyme layer is deposited by spray or dip coating, however, other methods of forming the enzyme layer may be used. The enzyme layer may be formed by dip coating and/or spray coating one or more layers at a predetermined concentration of the coating solution, insertion rate, dwell time, withdrawal rate, and/or desired thickness.

Flux Limiting Membrane

The sensor or sensor assembly may further include a membrane disposed over the subsequent layers described above, where the membrane alters or changes the rate of flux of one or more of the analytes of interest (e.g., "flux limiting membrane"). In aspects of the embodiments herein disclosed, the flux limiting membrane may substantially prevent or eliminate components of the sensor membrane (e.g., enzymes, proteins, carriers, reaction products or low molecular weight membrane-related compounds) from that which it is disposed over from contacting the subject or the subject's immune system. Thus, the flux limiting membrane may substantially "immobilize" the materials and components of the membrane layers it is disposed over. Although the following description is directed to a membrane for a glucose sensor, the membrane may be modified for other analytes and co-reactants as well. In one aspect, the sensor or sensor assembly includes a membrane as herein disclosed.

In one aspect, the membrane comprises a semi-permeable material that controls the flux of oxygen and glucose to the underlying enzyme layer, preferably providing oxygen in a non-rate-limiting excess. As a result, the upper limit of linearity of glucose measurement is extended to a much higher value than that which is achieved without the membrane. In one embodiment, the membrane exhibits an oxygen to glucose permeability ratio of from about 50:1 or less to about 400:1 or more, preferably about 200:1.

The material that comprises the membrane may be a vinyl polymer appropriate for use in sensor devices having sufficient permeability to allow relevant compounds to pass through it, for example, to allow an oxygen molecule to pass through in order to reach the active enzyme or electrochemical electrodes. Examples of materials which may be used to make the membrane include vinyl polymers having vinyl ester monomeric units. In a preferred embodiment, a flux limiting membrane comprises poly ethylene vinyl acetate (EVA polymer). In other aspects, the flux limiting membrane comprises poly(methylmethacrylate-co-butyl methacrylate) blended with the EVA polymer. The EVA polymer or its blends may be cross-linked, for example, with diglycidyl ether. Films of EVA are very elastomeric, which may provide resiliency to the sensor for navigating a tortuous path, for example, into venous anatomy.

In one aspect of the invention, the flux limiting membrane substantially excludes condensation polymers such as silicone and urethane polymers and/or copolymers or blends thereof. Such excluded condensation polymers typically contain residual heavy metal catalytic material that may otherwise be toxic if leached and/or difficult to completely remove, thus rendering their use in such sensors undesirable for safety and/or cost.

The EVA polymer may be provided from a source having a composition anywhere from about 9 wt % vinyl acetate (EVA-9) to about 40 wt % vinyl acetate (EVA-40). The EVA polymer is preferably dissolved in a solvent for dispensing on the sensor or sensor assembly. The solvent should be chosen for its ability to dissolve EVA polymer, to promote adhesion to the sensor substrate and enzyme electrode, and to form a solution that may be effectively applied (e.g. spray-coated or dip coated). Solvents such as cyclohexanone, paraxylene, and tetrahydrofuran may be suitable for this purpose. The solution may include about 0.5 wt % to about 6.0 wt % of the EVA polymer. In addition, the solvent should be sufficiently volatile to evaporate without undue agitation to prevent issues with the underlying enzyme, but not so volatile as to create problems with the spray process. In a preferred embodiment, the vinyl acetate component of the flux limiting membrane includes about 20% vinyl acetate. In preferred embodiments, the flux limiting membrane is deposited onto the enzyme layer to yield a layer thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 5, 5.5 or 6 microns to about 6.5, 7, 7.5 or 8 microns. The flux limiting membrane may be deposited onto the enzyme layer by spray coating or dip coating. In one aspect, the flux limiting membrane is deposited on the enzyme layer by dip coating a solution of from about 1 wt. % to about 5 wt. % EVA polymer and from about 95 wt. % to about 99 wt. % solvent.

In one aspect of the invention, an electrochemical analyte sensor is provided comprising a flux limiting membrane covering the enzyme layer, the interference layer and at least a portion of the electroactive surface. Thus, the sensor comprises at least one electroactive surface, an interference layer comprising an interference layer comprising a cellulosic derivative in contact with and at least partially covering at least a portion of the electroactive surface, an enzyme layer comprising a hydrophilic polymer-enzyme composition, at least a portion of the enzyme layer in contact with and at least partially covering the interference layer, and a flux limiting membrane covering the enzyme layer, the interference layer and at least a portion of the electroactive surface.

Bioactive Agents

In some alternative embodiments, a bioactive agent may be optionally incorporated into the above described sensor system, such that the bioactive diffuses out into the biological environment adjacent to the sensor. Additionally or alternately, a bioactive agent may be administered locally at the exit-site or implantation-site. Suitable bioactive agents include those that modify the subject's tissue response to any of the sensor or components thereof. For example, bioactive agents may be selected from anti-inflammatory agents, anti-infective agents, anesthetics, inflammatory agents, growth factors, immunosuppressive agents, antiplatelet agents, anticoagulants, anti-proliferates, ACE inhibitors, cytotoxic agents, anti-barrier cell compounds, vascularization-inducing compounds, anti-sense molecules, or mixtures thereof.

Flexible Substrate Sensor Assembly Adapted for Intravenous Insertion

In one aspect, an electrochemical analyte sensor assembly may be configured for an intravenous insertion to a vascular system of a subject. In order to accommodate the sensor within the confined space of a device suitable for intravenous insertion, the sensor assembly may comprise a flexible substrate, such as a flex circuit. For example, the flexible substrate of the flex circuit may be configured as thin conductive electrodes coated on a non-conductive material such as a thermoplastic or thermoset. Conductive traces may be formed on the non-conductive material and electrically coupled to the thin conductive electrodes. The electrodes of the flex circuit may be as described above wherein the traces and contacts of flex circuit supports and electrically couples to the electrodes.

The flex circuit may comprise at least one reference electrode and at least one working electrode, the at least one working electrode having an electroactive surface capable of providing a detectable electrical output upon interaction with an electrochemically detectable species. The flex circuit may further comprise at least one counter electrode. In one aspect, the flex circuit contains two or more working electrodes and two or more counter electrodes. In one aspect, the flex circuit contains two or more working electrodes, two or more blank electrodes and two or more counter electrodes.

An interference layer comprising a cellulosic derivative may be placed in direct contact with and at least partially covering a portion of the electroactive surface of working electrode of the flex circuit. An enzyme layer comprising a hydrophilic polymer-enzyme composition capable of enzymatically interacting with an analyte so as to provide the electrochemically detectable species, may be placed such that at least a portion thereof is in direct contact with and at least partially covering the interference layer. A membrane, such as a membrane that alters the flux of an analyte of interest may be placed such that it covers the hydrophilic polymeric layer, the interference layer and at least a portion of the electroactive surface of the flex circuit. The flex circuit preferably is configured to be electrically configurable to a control unit. An example of an electrode of a flex circuit and it construction is found in co-assigned U.S. Application Nos. 2007/0202672 and 2007/0200254, incorporated herein by reference in their entirety.

Medical devices adaptable to the sensor assembly as described above include, but are not limited to a central venous catheter (CVC), a pulmonary artery catheter (PAC), a probe for insertion through a CVC or PAC or through a peripheral IV catheter, a peripherally inserted catheter (PICC), Swan-Ganz catheter, an introducer or an attachment to a Venous Arterial blood Management Protection (VAMP) system. Any size/type of Central Venous Catheter (CVC) or intravenous devices may be used or adapted for use with the sensor assembly.

For the foregoing discussion, the implementation of the sensor or sensor assembly is disclosed as being placed within a catheter; however, other devices as described above are envisaged and incorporated in aspects of the invention. The sensor assembly will preferably be applied to the catheter so as to be flush with the OD of the catheter tubing or the sensor may be recessed. This may be accomplished, for example, by thermally deforming or skiving the OD of the tubing to provide a recess for the sensor. The sensor assembly may be bonded in place, and sealed with an adhesive (ie. urethane, 2-part epoxy, acrylic, etc.) that will resist bending/peeling, and adhere to the urethane CVC tubing, as well as the materials of the sensor. Small diameter electrical wires may be attached to the sensor assembly by soldering, resistance welding, or conductive epoxy. These wires may travel from the proximal end of the sensor, through one of the catheter lumens, and then to the proximal end of the catheter. At this point, the wires may be connected to an electrical connector, for example by solder or by ribbon cable with suitable connectors.

The sensor assembly as disclosed herein can be added to a catheter in a variety of ways. For example, an opening may be provided in the catheter body and a sensor or sensor assembly may be mounted inside the lumen at the opening so that the sensor would have direct blood contact. In one aspect, the sensor or sensor assembly may be positioned proximal to all the infusion ports of the catheter. In this configuration, the sensor would be prevented from or minimized in measuring otherwise detectable infusate concentration instead of the blood concentration of the analyte. Another aspect, an attachment method may be an indentation on the outside of the catheter body and to secure the sensor inside the indentation. This may have the added advantage of partially isolating the sensor from the temperature effects of any added infusate. Each end of the recess may have a skived opening to 1) secure the distal end of the sensor and 2) allow the lumen to carry the sensor wires to the connector at the proximal end of the catheter.

Preferably, the location of the sensor assembly in the catheter will be proximal (upstream) of any infusion ports to prevent or minimize IV solutions from affecting analyte measurements. In one aspect, the sensor assembly may be about 2.0 mm or more proximal to any of the infusion ports of the catheter.

In another aspect, the sensor assembly may be configured such that flushing of the catheter (ie. saline solution) may be employed in order to allow the sensor assembly to be cleared of any material that may interfere with its function.

Sterilization of the Sensor or Sensor Assembly

Generally, the sensor or the sensor assembly as well as the device that the sensor is adapted to are sterilized before use, for example, in a subject. Sterilization may be achieved using radiation (e.g., electron beam or gamma radiation), ethylene oxide or flash-UV sterilization, or other means known in the art.

Disposable portions, if any, of the sensor, sensor assembly or devices adapted to receive and contain the sensor preferably will be sterilized, for example using e-beam or gamma radiation or other know methods. The fully assembled device or any of the disposable components may be packaged inside a sealed non-breathable container or pouch.

Referring now to the Figures, FIG. 1 is an amperometric sensor 11 in the form of a flex circuit that incorporates a sensor embodiment disclosed herein. The sensor or sensor 11 may be formed on a substrate 13 (e.g., a flex substrate, such as copper foil laminated with polyimide). One or more electrodes 15, 17 and 19 may be attached or bonded to a surface of the substrate 13. The sensor 11 is shown with a reference electrode 15, a counter electrode 17, and a working electrode 19. In another embodiment, one or more additional working electrodes may be included on the substrate 13. Electrical wires 210 may transmit power to the electrodes for sustaining an oxidation or reduction reaction, and may also carry signal currents to a detection circuit (not shown) indicative of a parameter being measured. The parameter being measured may be any analyte of interest that occurs in, or may be derived from, blood chemistry. In one embodiment, the analyte of interest may be hydrogen peroxide, formed from reaction of glucose with glucose oxidase, thus having a concentration that is proportional to blood glucose concentration.

FIG. 2 depicts a cross-sectional side view of a portion of substrate 13 in the vicinity of the working electrode 19 of an embodiment disclosed herein. The working electrode 19 may be at least partially coated with an interference layer 50. Interference layer 50 may be at least partially coated with an enzyme layer 23 that is selected to chemically react when the sensor is exposed to certain reactants, for example, found in the bloodstream. For example, in an embodiment for a glucose sensor, enzyme layer 23 may contain glucose oxidase, such as may be derived from *Aspergillus niger* (EC 1.1.3.4), for example, type II, type VII, or type X.

FIG. 3 shows a cross sectional side view of the working electrode site on the sensor substrate 13 further comprising flux limiting membrane 25 covering enzyme layer 23 and interference layer 50 and at least a portion of electrode 19. Flux limiting membrane 25 may selectively allow diffusion, from blood to the enzyme layer 23, a blood component that reacts with the enzyme. In a glucose sensor embodiment, the flux limiting membrane 25 passes an abundance of oxygen, and selectively limits glucose, to the enzyme layer 23. In addition, a flux limiting membrane 25 that has adhesive properties may mechanically seal the enzyme layer 23 to the sub-layers and/or working electrode 19, and may also seal the working electrode 19 to the sensor substrate 13. It is herein disclosed that a flux limiting membrane formed from an EVA polymer may serve as a flux limiter at the top of the electrode, but also serve as a sealant or encapsulant at the enzyme/electrode boundary and at the electrode/substrate boundary. An additional biocompatible layer (not shown), including a biocompatible anti-thrombotic substance such as heparin, may be added onto the flux limiting membrane 25.

Referring now to FIGS. 4-5, aspects of the sensor adapted to a central line catheter with a sensor or sensor assembly are discussed as exemplary embodiments, without limitation to any particular intravenous device. FIG. 4 shows a sensor assembly within a multilumen catheter. The catheter assembly 10 may include multiple infusion ports 11*a*, 11*b*, 11*c*, 11*d* and one or more electrical connectors 130 at its most proximal end. A lumen 15*a*, 15*b*, 15*c* or 15*d* may connect each infusion port 11*a*, 11*b*, 11*c*, or 11*d*, respectively, to a junction 190. Similarly, the conduit 170 may connect an electrical connector 130 to the junction 190, and may terminate at junction 190, or at one of the lumens 15*a*-15*d* (as shown). Although the particular embodiment shown in FIG. 4 is a multilumen catheter having four lumens and one electrical connector, other embodiments having other combinations of lumens and connectors are possible, including a single lumen catheter, a catheter having multiple electrical connectors, etc. In another embodiment, one of the lumens and the electrical connector may be reserved for a probe or other sensor mounting device, or one of the lumens may be open at its proximal end and designated for insertion of the probe or sensor mounting device.

The distal end of the catheter assembly 10 is shown in greater detail in FIG. 5. At one or more intermediate locations along the distal end, the tube 21 may define one or more ports formed through its outer wall. These may include the intermediate ports 25*a*, 25*b*, and 25*c*, and an end port 25*d* that may be formed at the distal tip of tube 21. Each port 25*a*-25*d* may correspond respectively to one of the lumens 15*a*-15*d*. That is, each lumen may define an independent channel extending from one of the infusion ports 11*a*-11*d* to one of the tube ports 25*a*-25*d*. The sensor assembly may be presented to the sensing environment via positioning at one or more of the ports to provide contact with the medium to be analyzed.

Central line catheters may be known in the art and typically used in the Intensive Care Unit (ICU)/Emergency Room of a hospital to deliver medications through one or more lumens of the catheter to the patient (different lumens for different medications). A central line catheter is typically connected to an infusion device (e.g. infusion pump, IV drip, or syringe port) on one end and the other end inserted in one of the main arteries or veins near the patient's heart to deliver the medications. The infusion device delivers medications, such as, but not limited to, saline, drugs, vitamins, medication, proteins, peptides, insulin, neural transmitters, or the like, as needed to the patient. In alternative embodiments, the central line catheter may be used in any body space or vessel such as intraperitoneal areas, lymph glands, the subcutaneous, the lungs, the digestive tract, or the like and may determine the analyte or therapy in body fluids other than blood. The central line catheter may be a double lumen catheter. In one aspect, an analyte sensor is built into one lumen of a central line catheter and is used for determining characteristic levels in the blood and/or bodily fluids of the user. However, it will be recognized that further embodiments may be used to determine the levels of other agents, characteristics or compositions, such as hormones, cholesterol, medications, concentrations, viral loads (e.g., HIV), or the like. Therefore, although aspects disclosed herein may be primarily described in the context of glucose sensors used in the treatment of diabetes/diabetic symptoms, the aspects disclosed may be applicable to a wide variety of patient treatment programs where a physiological characteristic is monitored in an ICU, including but not limited to blood gases, pH, temperature and other analytes of interest in the vascular system.

In another aspect, a method of intravenously measuring an analyte in a subject is provided. The method comprises providing a catheter comprising the sensor assembly as described herein and introducing the catheter into the vascular system of a subject. The method further comprises measuring an analyte.

EXAMPLES

Preparation of Controls: Controls were prepared having a layer of dried PBS deposited between the electroactive surface and the interference layer (CAB) and excluding a PVP layer. Thus, to the electroactive surface of a working electrode treated with a 3 wt % ethanol solution of 3-glycidoxypropyl trimethoxysilane and dried, was deposited an aqueous PBS solution [137 mM NaCl, 2.7 mM KCl, 10 mM phosphate] and dried. To the PBS layer was coated an interference layer of 0.2 wt % CAB solution in cyclohexanone and dried for 15 minutes @ 60 C. A second PBS layer was deposited on the CAB layer as above. The enzyme layer was deposited from a solution prepared as follows: To an aliquot of a stock solution of 60 mg GOx and 140 mg BSA was added 100 microliters of 20 wt % PEG and 160 microliters of glycerol in 4 ml of acetate buffered DI water. The pH of the solution was adjusted to about 6 with 1M sodium bicarbonate. 25% glutaraldehyde solution (10 microliters for each ml of solution) was combined prior to deposition and the enzyme layer was immobilized on the CAB layer and dried overnight at RT. A flux limiting membrane comprising a 2 wt % EVA in xylene was sprayed over the enzyme layer and dried for 15 minutes @ 60 C.

Comparative examples 1-6, were prepared as described above for the controls samples, except a separate PVP layer was deposited on the electroactive surface (between electroactive surface and the CAB) and a separate PVP layer was deposited between the CAB and the enzyme layer. Thus, to the electroactive surface of a working electrode treated with a 3 wt % ethanol solution of 3-glycidoxypropyl trimethoxysilane and dried, was deposited a 3.75 wt % PVP solution in PBS followed by the deposition of an interference layer of 0.2 wt % CAB solution in cyclohexanone and dried for 15 minutes @ 60 C. A separate PVP layer was deposited from a 3.75 wt % PVP solution in PBS on the CAB layer and dried. The enzyme layer was deposited to the above layer from a solution prepared as follows: A solution of 30 mg GOx and 70 mg BSA was added to 2 microliters of 2.5 wt % K90 PVP in acetate buffered DI water. The pH of the solution was adjusted to about 6 with 1M sodium bicarbonate. 25% glutaraldehyde solution (10 microliters for each ml of solution) was combined prior to deposition and immobilized on the CAB layer and may be structurally designated as "electrode/3.75PVP/CAB/3.75PVP/2.5PVP-GOx". Likewise, a solution of 30 mg GOx and 70 mg BSA was added to 2 microliters of 5 wt % K90 PVP in acetate buffered DI water. The pH of the solution was adjusted to about 6 with 1M sodium bicarbonate. Glutaraldehyde solution 25 wt % (10 microliters for each ml of solution) was combined with the enzyme solution prior to deposition and immobilized on the CAB layer and may be structurally designated as "electrode/3.75PVP/CAB/3.75PVP/5PVP-GOx." A flux limiting membrane comprising a 2 wt % EVA in xylene was sprayed over the enzyme layer of these examples and dried for 15 minutes @ 60 C.

Comparative examples 7-8, were prepared as described above for the controls samples, except a separate PVP layer was deposited from a 2.5 wt % PVP solution in distilled water (dH2O) followed by the deposition of an interference layer of 0.2 wt % CAB solution in cyclohexanone and dried for 15 minutes @ 60 C. A separate PVP layer was deposited from a 2.5 wt % PVP solution in distilled water (dH2O) on the CAB layer and dried. The enzyme layer was deposited to the above layer from a solution prepared as follows: A solution of 30 mg GOx and 70 mg BSA was added to 2 microliters of 2.5 wt % K90 PVP in acetate buffered DI water. The pH of the solution was adjusted to about 6 with 1M sodium bicarbonate. 25% glutaraldehyde solution (10 microliters for each ml of solution) was combined prior to deposition and immobilized on the CAB layer and may be structurally designated as "electrode/2.5PVP/CAB/2.5PVP/2.5PVP-GOx". Likewise, a solution of 30 mg GOx and 70 mg BSA was added to 2 microliters of 5 wt % K90 PVP in acetate buffered DI water. The pH of the solution was adjusted to about 6 with 1M sodium bicarbonate. Glutaraldehyde solution 25 wt % (10 microliters for each ml of solution) was combined with the enzyme solution prior to deposition and immobilized on the CAB layer and may be structurally designated as "electrode/2.5PVP/CAB/2.5PVP/5PVP-GOx." A flux limiting membrane comprising a 2 wt % EVA in xylene was sprayed over the enzyme layer of these examples and dried for 15 minutes @ 60 C.

Preparation of Exemplary Sensors

Exemplary sensors were prepared as the comparative examples except without a separate intervening PVP layer (or PBS layer) deposited below or above the CAB layer. Thus, exemplary sensors with an enzyme layer comprising 2.5 wt % and 5.0 wt % PVP-GOx were prepared and may be designated having the structure "electrode/CAB/2.5PVP-GOx" and "electrode/CAB/5PVP-GOx" respectively. A flux limiting membrane comprising a 2 wt % EVA in xylene was sprayed over the enzyme layer and dried for 15 minutes @ 60 C as above, to provide Test Sensors A having 2.5 wt % PVP-GOx. The enzyme layer of Test Sensors B comprised 5.0 wt % PVP.

Glucose sensor assemblies for the controls, comparative examples and exemplary sensors above were built, each including a blank electrode having BSA in the enzyme layer (5 wt %) without GOx and tested. Table 1 summarizes the controls and exemplary sensors described above.

The sensors were then connected to a potentiostat using a working electrode potential of about 850 mV for 10 minutes before adjusting the voltage to the working potential of about 650 mV .vs. Ag/AgCl prior to testing. The step change in the graphs represent a change in concentration of glucose.

TABLE 1

| | Dried PBS layer on electrode and on CAB layer | wt. % PVP in PBS deposited on electrode and CAB layer | wt. % PVP in DI water deposited on electrode and CAB layer | wt. % PVP in GOx enzyme layer | wt. % PEG in GOx enzyme layer |
|---|---|---|---|---|---|
| | Controls | | | | |
| | Yes | N/A | N/A | N/A | 20 |
| | Comparative Examples | | | | |
| 1 | Yes | 3.75 | N/A | 2.50 | N/A |
| 2 | Yes | 3.75 | N/A | 5.00 | N/A |
| 3 | Yes | 7.50 | N/A | 5.00 | N/A |
| 4 | Yes | 7.50 | N/A | 2.50 | N/A |
| 5 | Yes | 15 | N/A | 2.50 | N/A |
| 6 | Yes | 15 | N/A | 5.00 | N/A |
| 7 | Yes | N/A | 2.50 | 2.50 | N/A |
| 8 | Yes | N/A | 2.50 | 5.00 | N/A |
| | Exemplary Sensors | | | | |
| A | No | N/A | N/A | 2.50 | N/A |
| B | No | N/A | N/A | 5.00 | N/A |

Additional experiments were conducted to determine the effects of hydration/de-hydration and repetitive use on the observed break-in for sensors disclosed herein. For example, control sensors and comparative examples were exposed to a PBS solution, then exposed to increasing concentrations of glucose to assess glucose sensitivity. Then the sensors were immersed in PBS or water to remove glucose and test solution residuals. Subsequently, the sensors were desiccated to facilitate their dehydration. After storage in a dessicator for about 2 days or more, the sensors were immersed in PBS and their break-in and glucose sensitivity determined. These experiments showed break-in and sensitivity of the sensors remained substantially constant upon hydration/re-hydration for the sensors tested. Thus, break-in data obtained for control sensors and comparative example after dehydration and storage is essentially equivalent to first use data.

Figure 7:
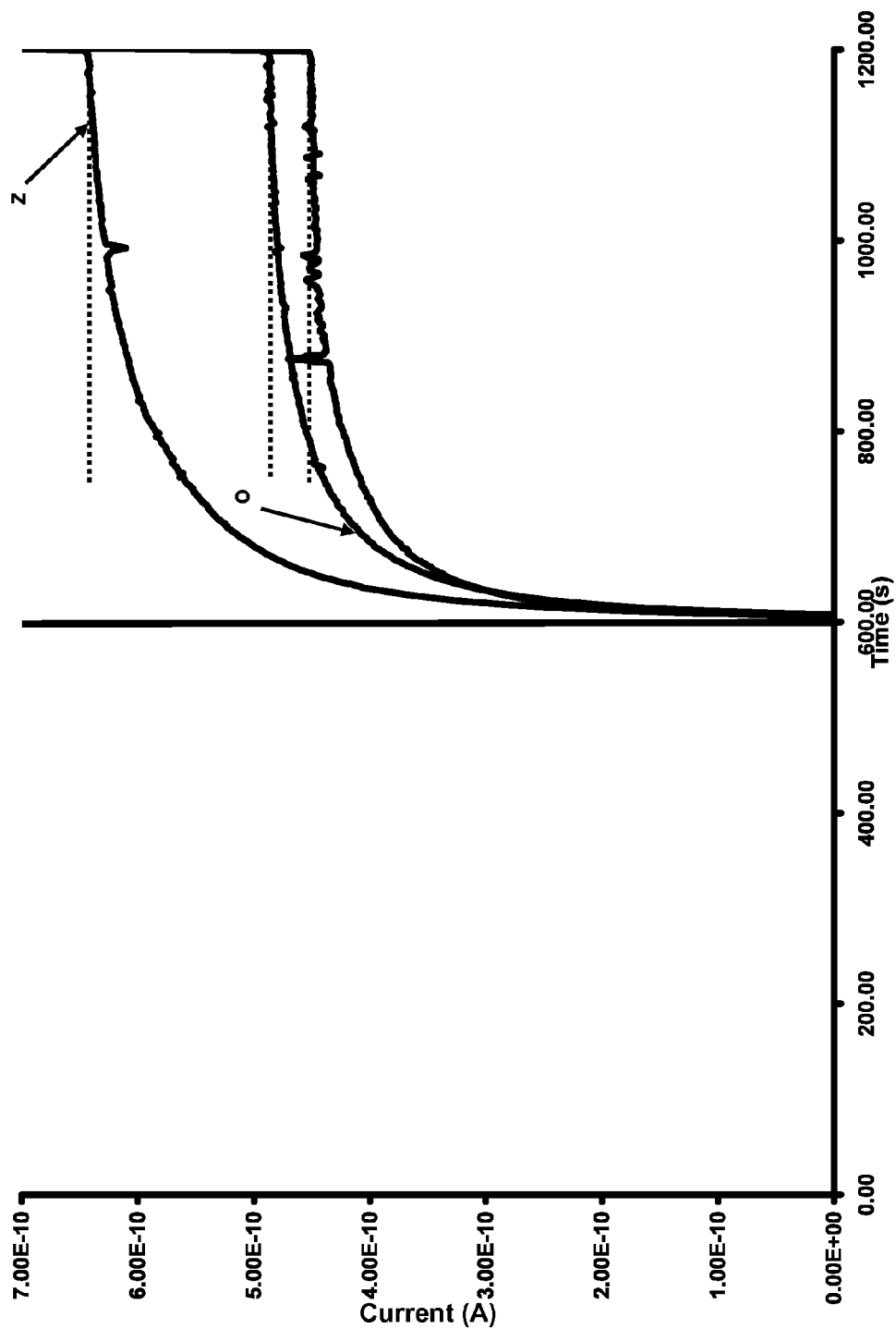
FIG. 7 is a graph of current output over time for a comparative sensor verses control during a first use.

FIGS. 6-7 are graphical representations showing first use response data of the controls (FIG. 6) and comparative examples 1-2 as described above (FIG. 7), and their corresponding current verses time after deployment. In FIG. 7, the comparative example with 5 wt % PVP in the enzyme layer is indicated by Arrow "O." The x-axis represents time, the y-axis represents current. The sensors were subjected to a PBS solution at pH 7.4 at 37° C. The sensors were then connected to a potentiostat using a working electrode potential of about 850 mV for 10 minutes before adjusting the voltage to the working potential of about 650 mV .vs. Ag/AgCl prior to testing. Arrow labeled "Z" on the horizontal dotted line represents the point tangent to the output curve, signifying the approximate break-in time. As seen in the graphs, the current of the comparative examples and the controls continues to increase over time, at least for about 30 minutes or more before obtaining break-in.

Figure 8:
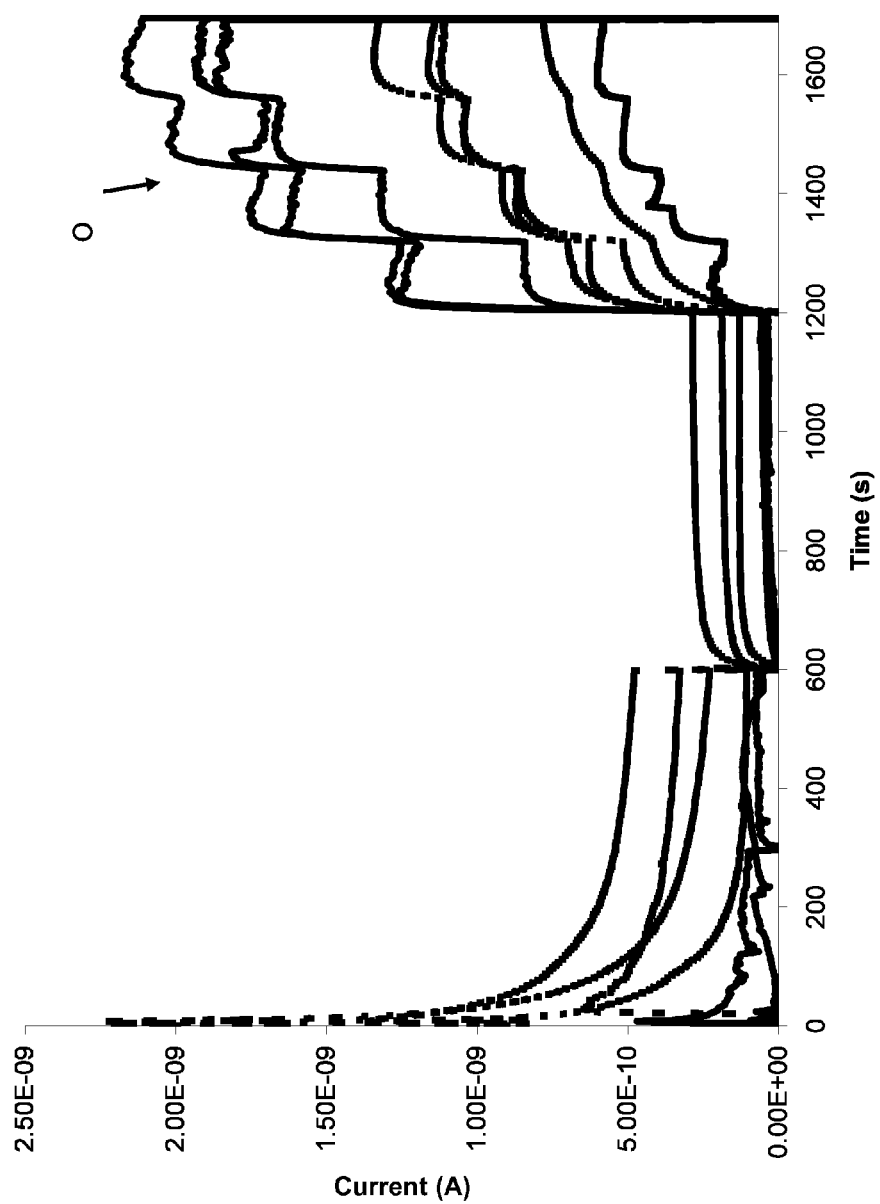
FIG. 8 is a graph of current output over time with step changes in concentration of glucose for a comparative sensor verses control.

FIG. 8 is a graphical representation showing response data to known glucose concentrations over time of the glucose sensors as depicted in FIGS. 6-7. The sample containing 5.0 wt % PVP in the enzyme layer is indicated by arrow "O." The x-axis represents time, the y-axis represents current. The sensors were subjected to a PBS solution at pH 7.4 at 37° C.

Figure 9:
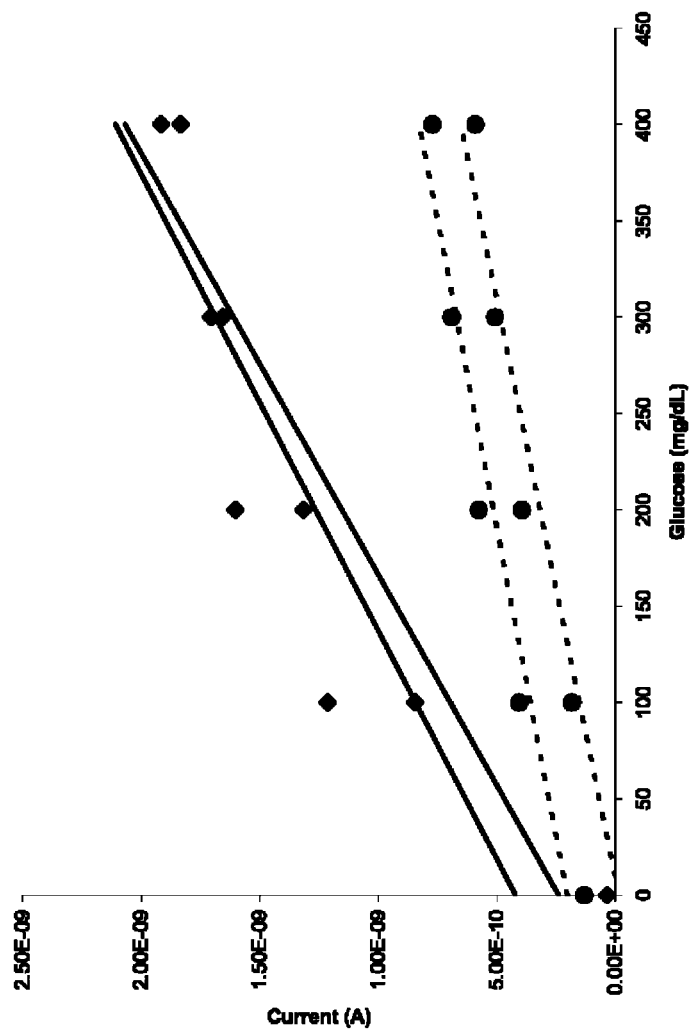
FIG. 9 is a calibration curve of current output verses glucose concentration for a comparative sensor verses control.
Figure 10:
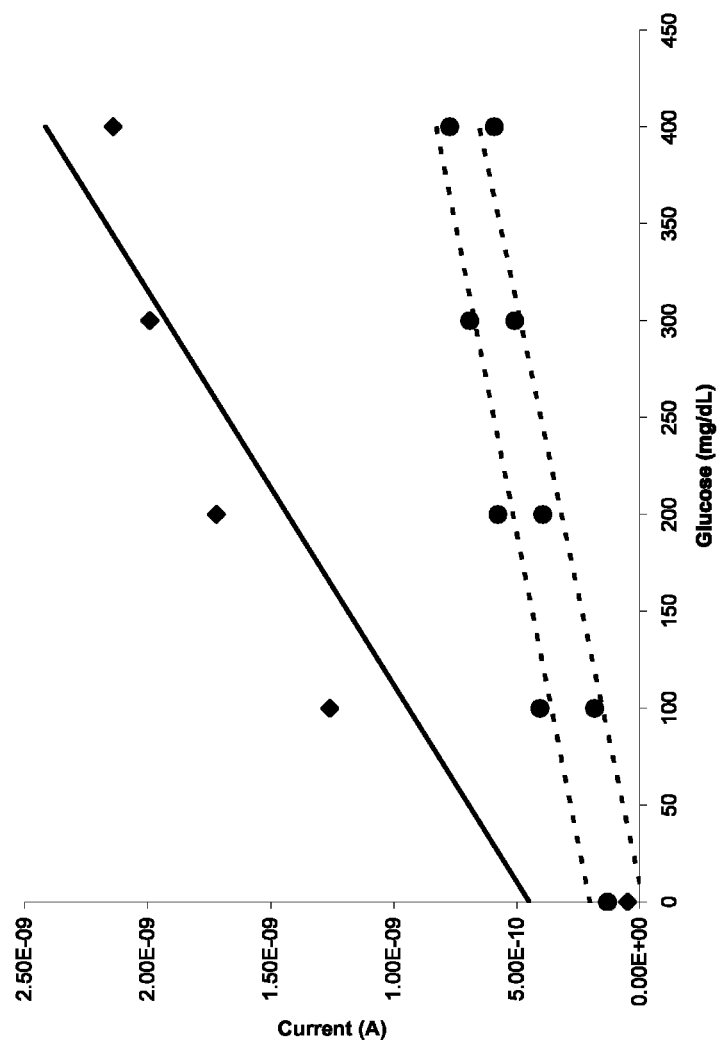
FIG. 10 is a calibration curve of current output verses glucose concentration for a comparative sensor verses control.

FIGS. 9-10 are graphical representations showing calibration curves of the comparative glucose sensors verses controls, as depicted in FIG. 8. In these graphs, controls are indicated by circles with dotted regression lines, and the comparative example sensors are indicated by diamonds with solid regression lines.

Figure 11:
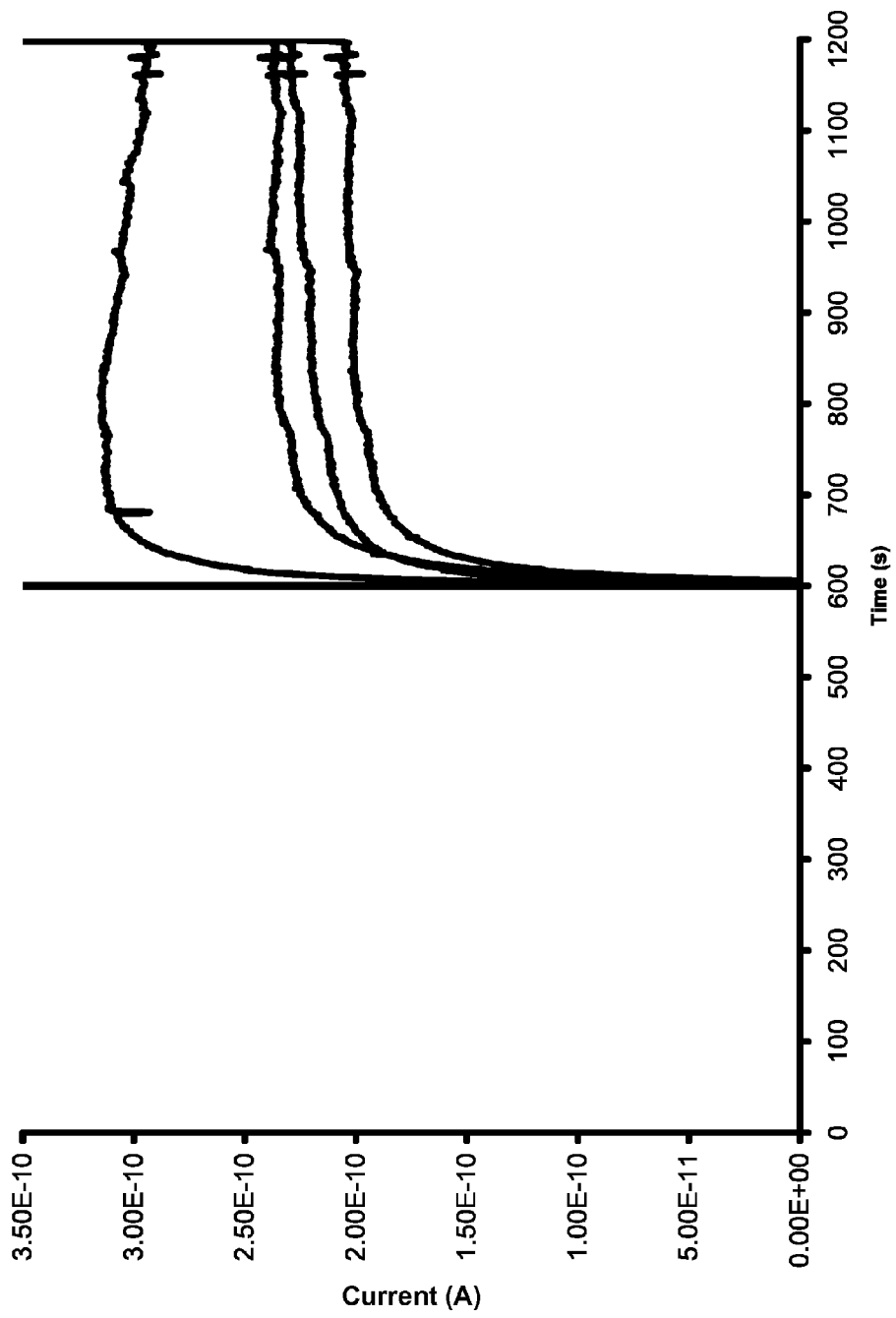
FIG. 11 is a graph of current output over time for controls during a first use.
Figure 12:
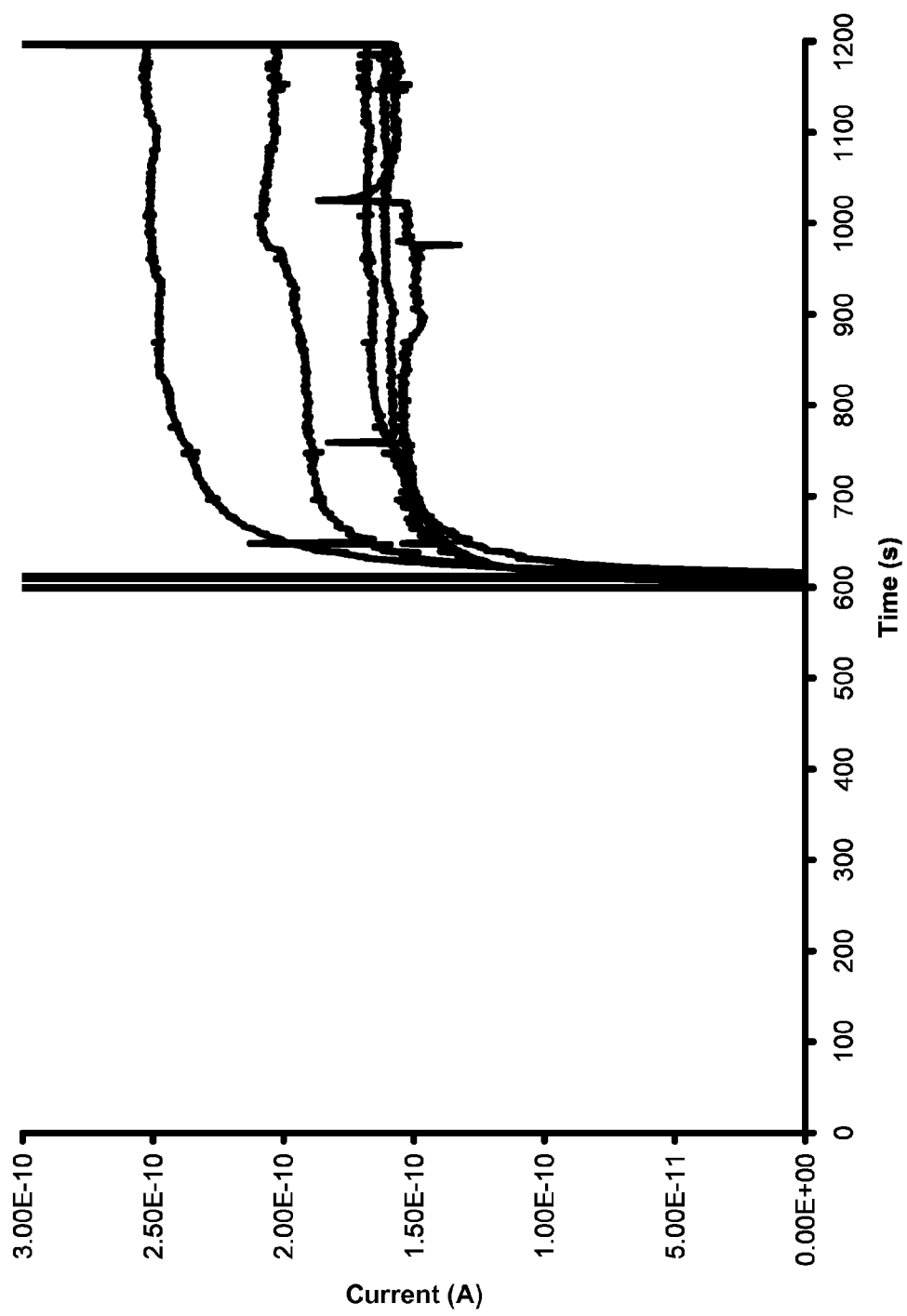
FIG. 12 is a graph of current output over time for a comparative sensor during a first use.
Figure 13:
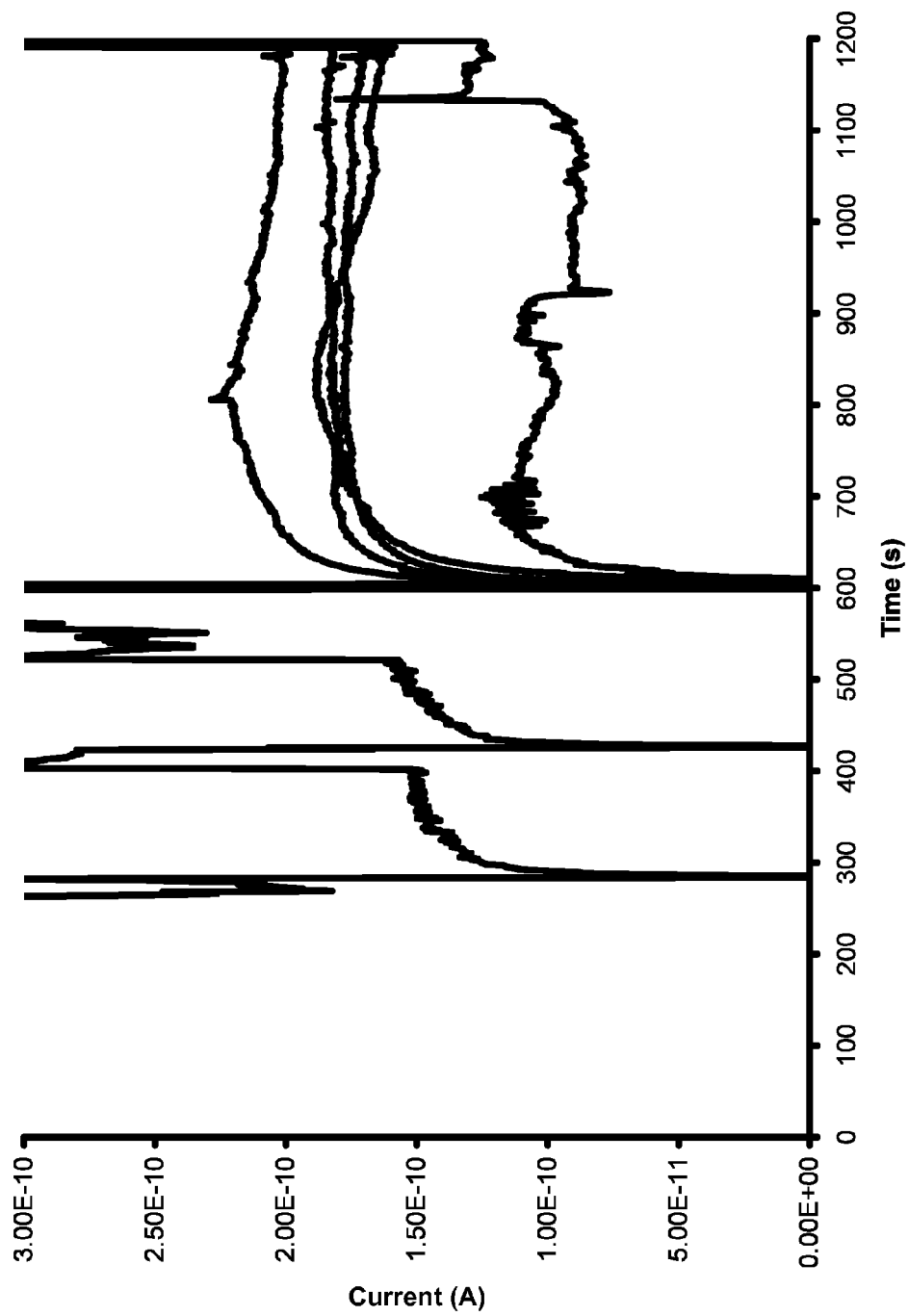
FIG. 13 is a graph of current output verses time for a comparative sensor during a first use.

FIGS. 11-13 are graphical representations showing first use response data of controls (FIG. 11) and comparative examples 7-8 (FIGS. 12-13 respectively), and their corresponding current verses time after deployment, as described above. In these graphs, controls are indicated by dotted lines, and comparative sensors are indicated by solid lines. The x-axis represents time, the y-axis represents current. The sensors were subjected to a PBS solution at pH 7.4 at 37° C. for determining break-in. The sensors were connected to a potentiostat using a working electrode potential of about 850 mV for 10 minutes before adjusting the voltage to the working potential of about 650 mV .vs. Ag/AgCl prior to testing. As seen in the graphs, the current continues to increase over time, at least for about 30 minutes from deployment for the controls and some of the comparative examples, while only a few of the comparative examples having a separate intervening PVP layer (or PBS) deposited below or above the CAB layer demonstrated constant current output close to 30 minutes from deployment.

Figure 14:
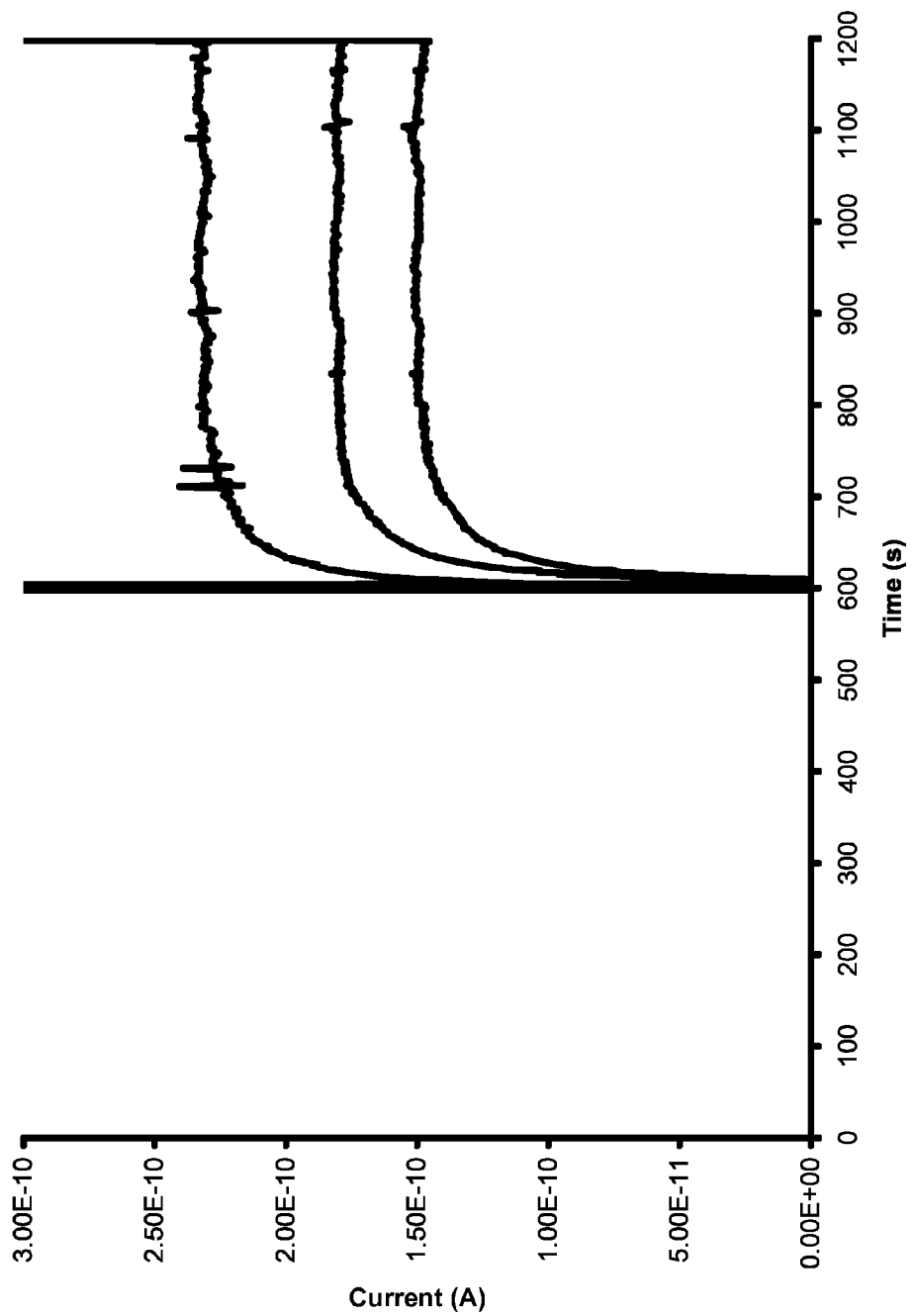
FIGS. 14 and 14A are graphs of current output over time for sensor embodiments of the invention during a first use.
Figure 14A:
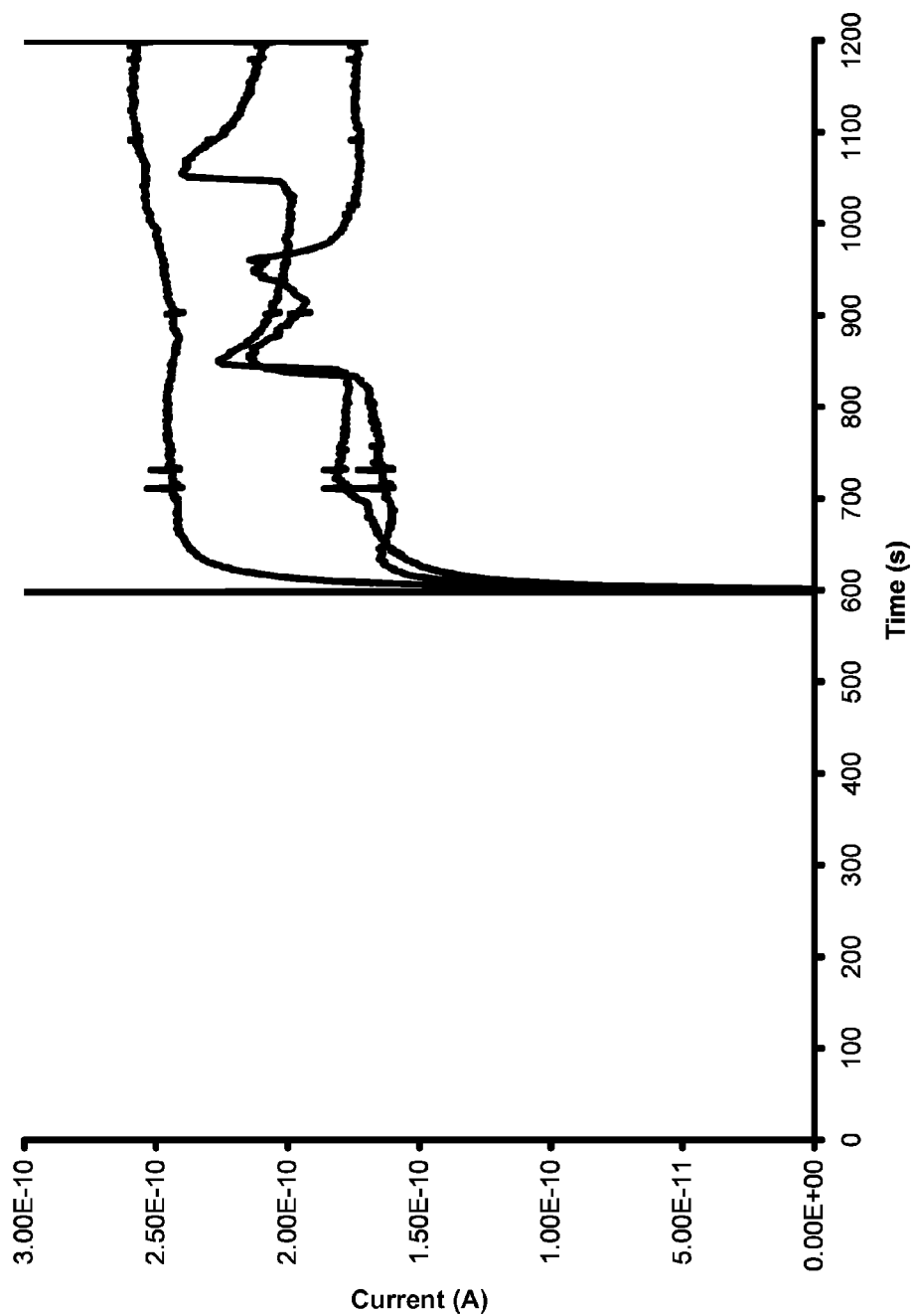

FIGS. 14 and 14A are graphical representations showing current verses time of first use response data for exemplary sensor embodiments A and B. The x-axis represents time, the y-axis represents current. The sensors were subjected to a PBS solution at pH 7.4 at 37° C. The sensors were then connected to a potentiostat using a working electrode potential of about 850 mV for 10 minutes before adjusting the voltage to the working potential of about 650 mV .vs. Ag/AgCl prior to testing As seen in the graphs, the exemplary sensor embodiments without a separate intervening PVP layer (or PBS) deposited below or above the CAB layer rapidly achieved a constant current output within about 30 minutes or less from deployment, whereas the current continues to increase over time for at least for more than about 30 minutes from deployment for the controls and most of the comparative examples described above.

Figure 15:
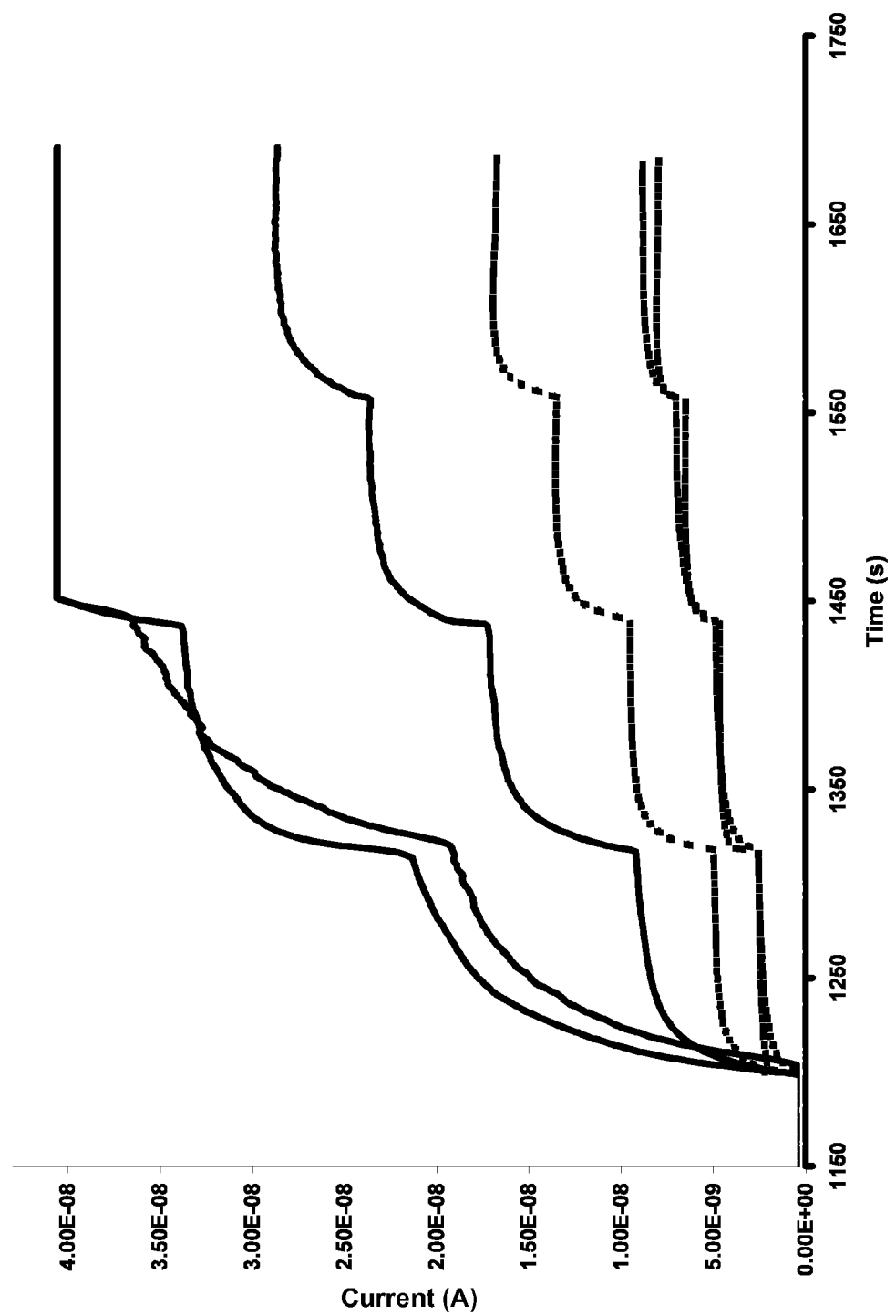
FIG. 15 is a graph of current output over time with a step change in concentration of glucose for a comparative sensor verses control.
Figure 16:
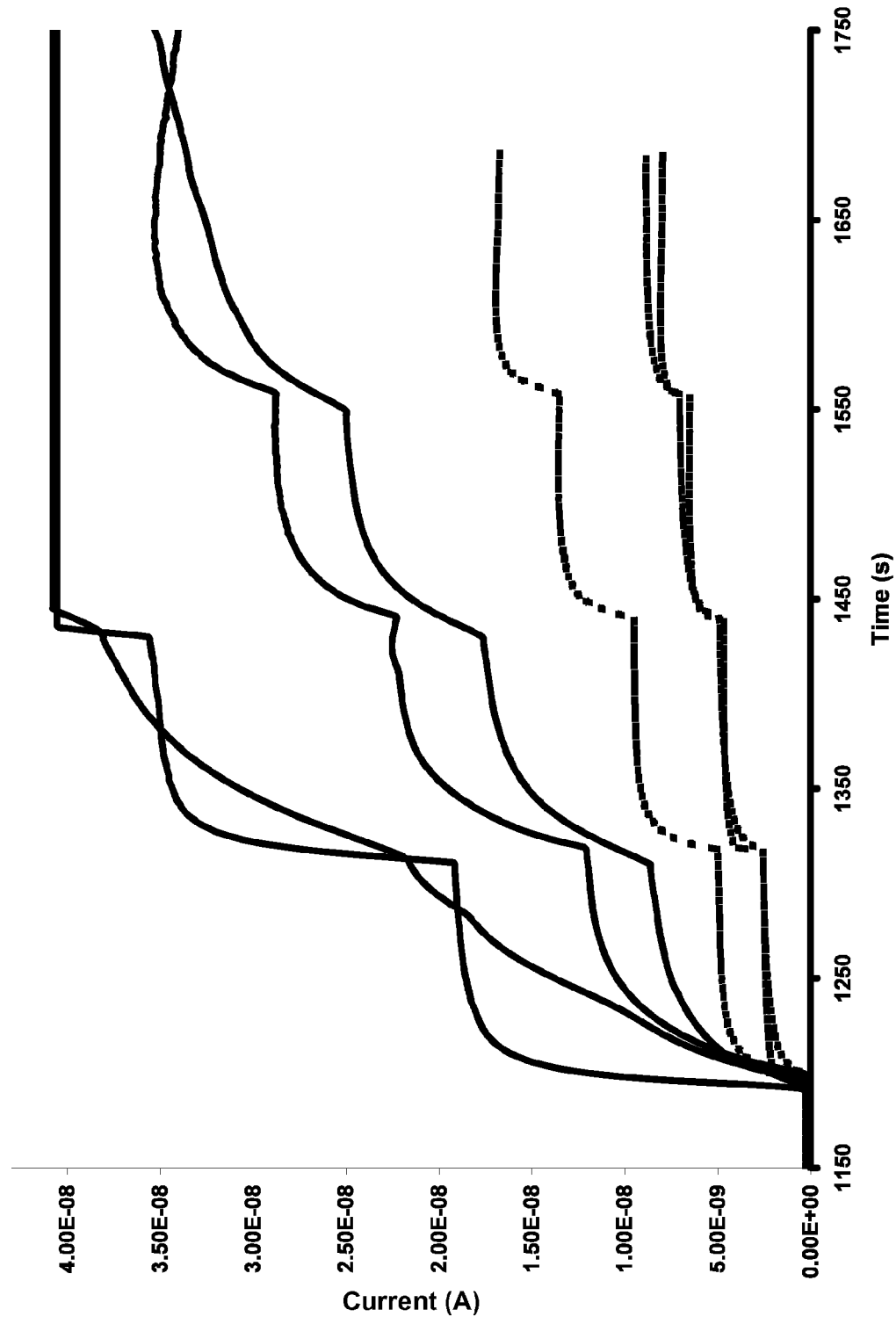
FIG. 16 is a graph of current output over time with a step change in concentration of glucose for a comparative sensor verses control.
Figure 17:
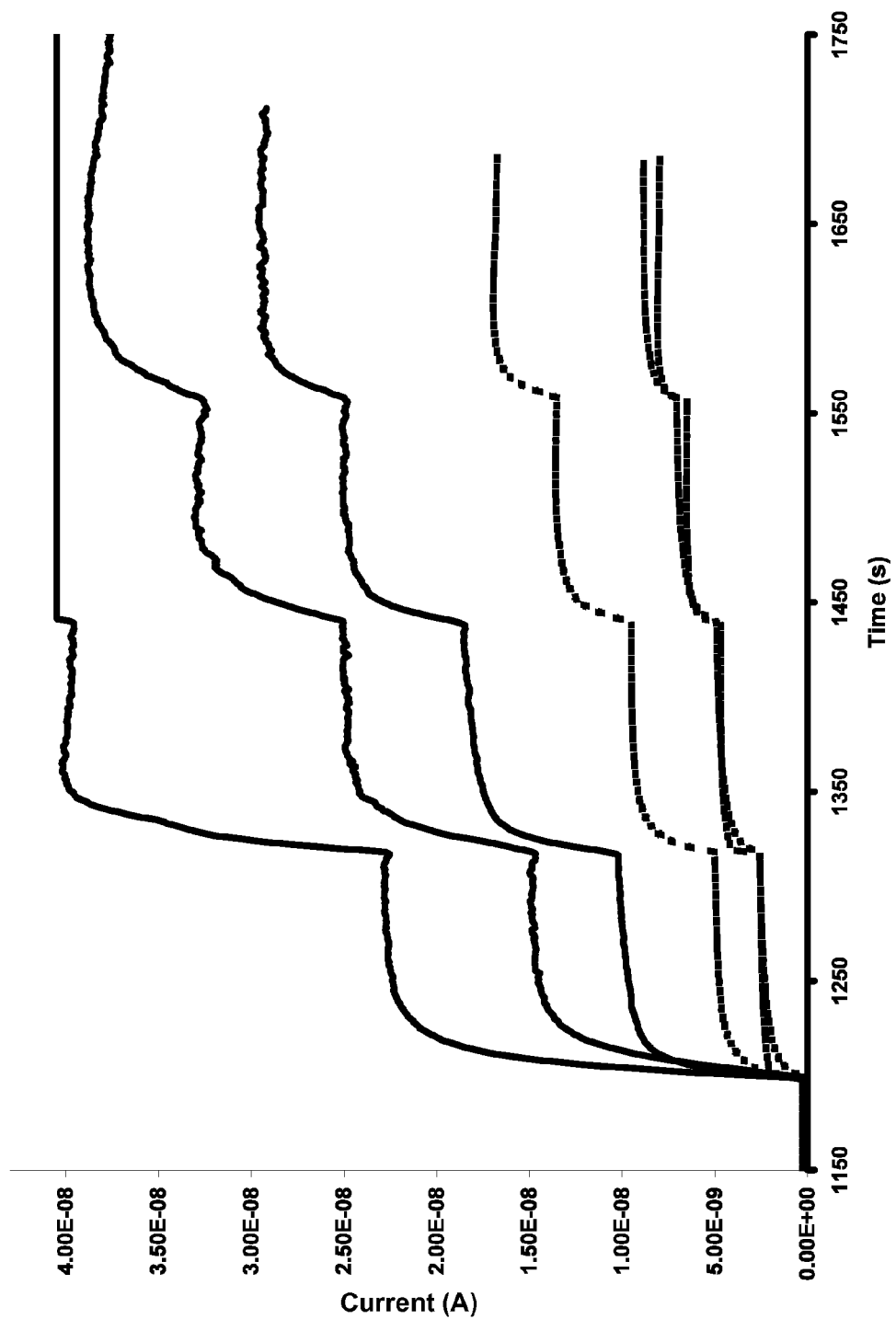
FIG. 17 is a graph of current output over time with a step change in concentration of glucose for a sensor embodiment of the invention verses control.
Figure 18:
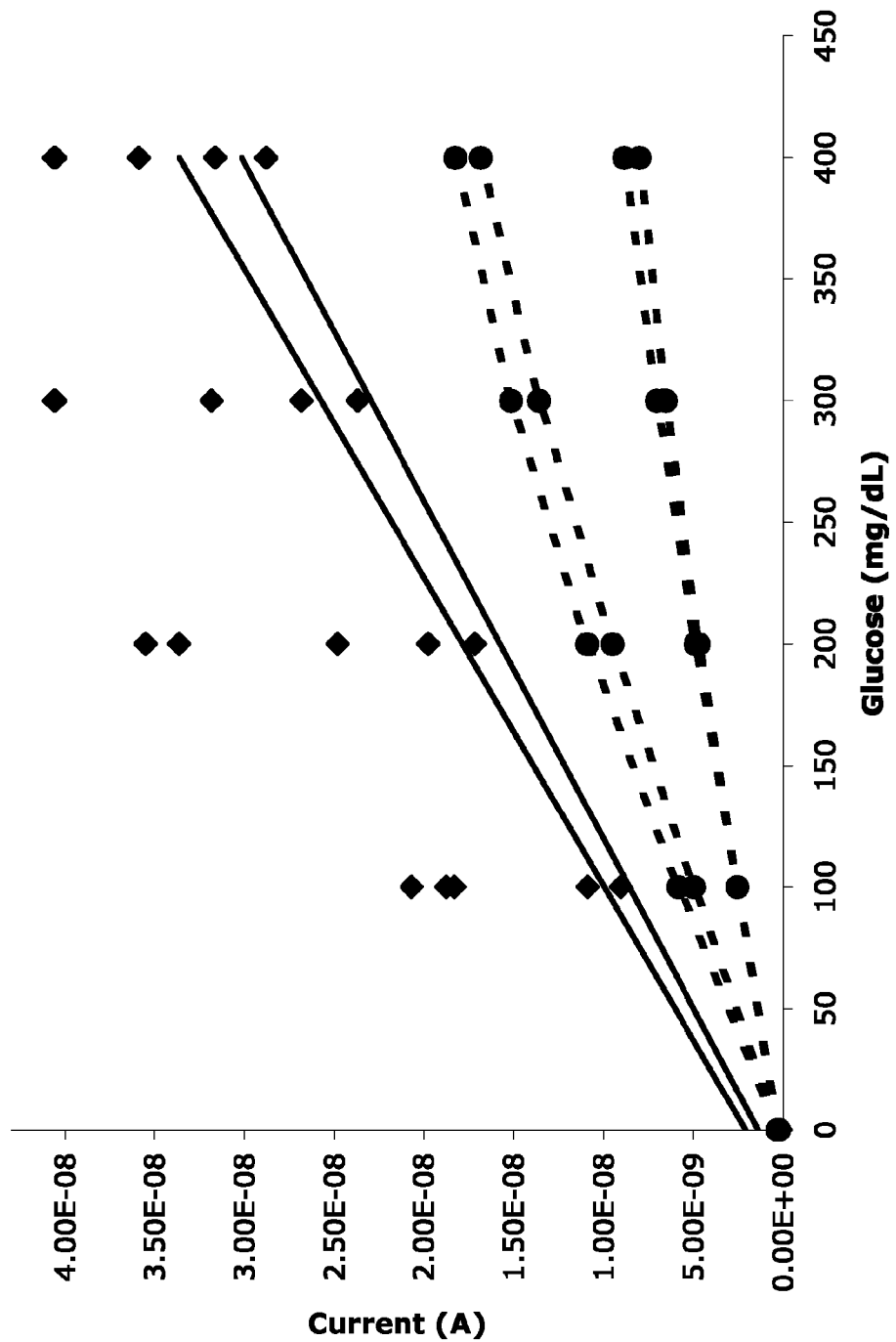
FIG. 18 is a calibration curve of current output verses glucose concentration for a comparative sensor verses control.
Figure 19:
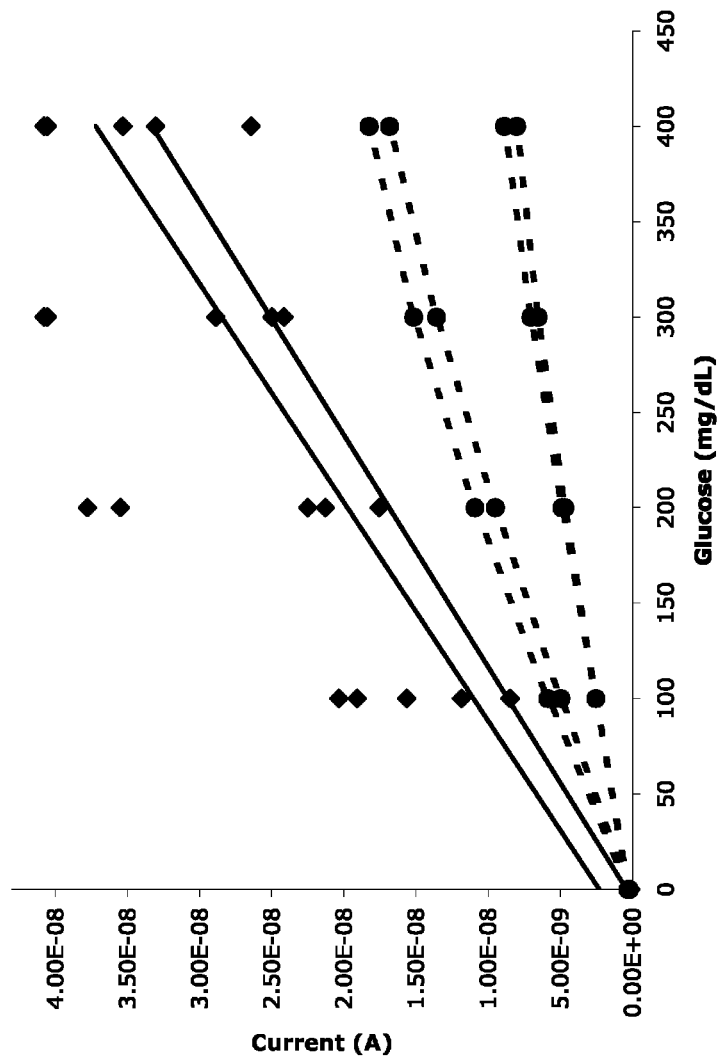
FIG. 19 is a calibration curve of current output verses glucose concentration for a comparative sensor verses control.
Figure 20:
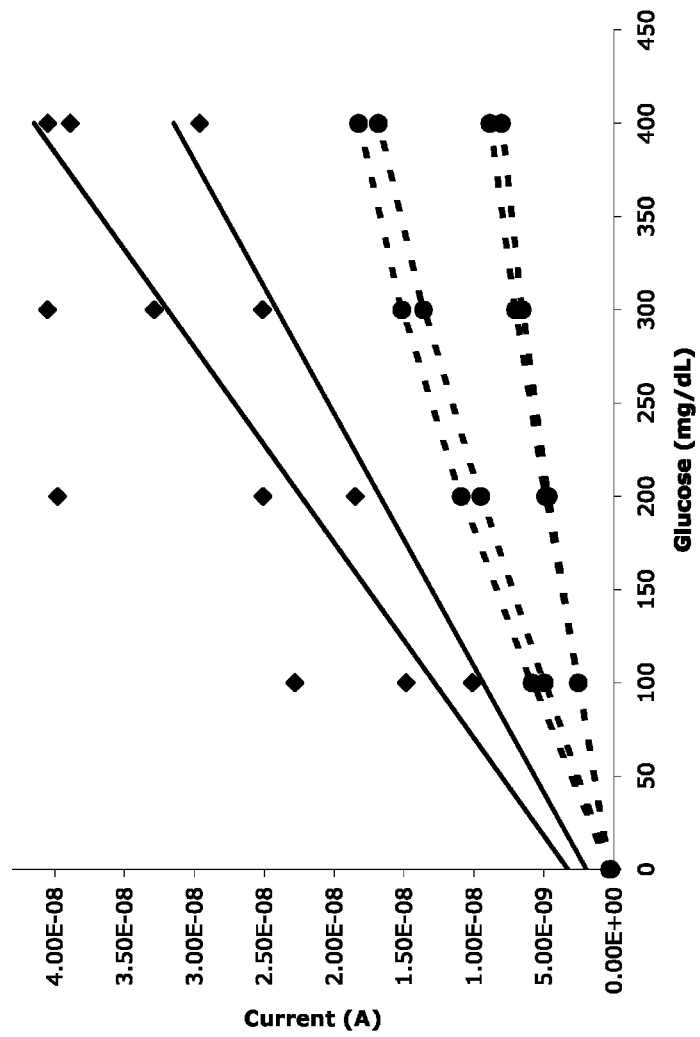
FIGS. 20 and 20A are calibration curves of current output verses glucose concentration for sensor embodiments of the invention verses control.
Figure 20A:
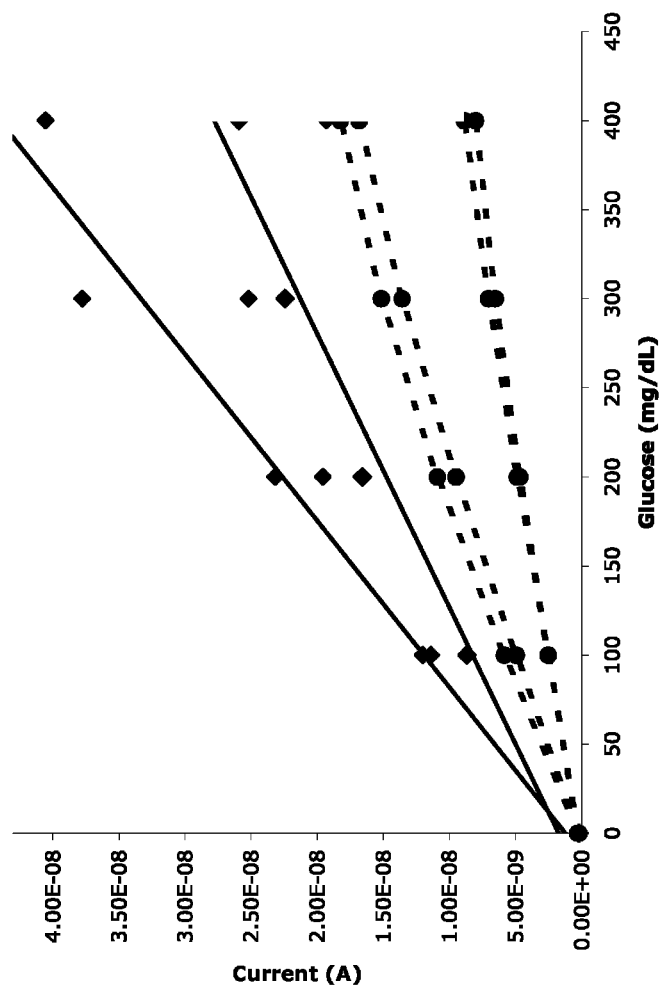

FIGS. 15-17 are graphical representations showing response data to known glucose concentration values over time of the glucose sensors as depicted in FIGS. 11-14, respectively. In these graphs, controls are indicated by dotted lines, and comparative or exemplary sensors are indicated by solid lines. The x-axis represents time, the y-axis represents current. The sensors were connected to a potentiostat using a working electrode potential of about 850 mV for about 10 minutes before adjusting the voltage to the working potential of about 650 mV .vs. Ag/AgCl prior to testing. The sensors were subjected to a PBS solution at pH 7.4 at 37° C. and the glucose solutions were added. The step change in the graphs represent a change in concentration of glucose.

FIGS. 18-19 and 20-20A are graphical representations showing calibration curves of the comparative glucose sensors 7-8 (FIGS. 18-19, respectively), and of the exemplary sensors A and B embodiments (FIGS. 20-20A), verses controls. In these graphs, controls are indicated by circles with dotted regression lines, and the comparative example sensors or the exemplary sensors are indicated by diamonds with solid regression lines. Accordingly, accurate measurement of glucose concentration is achievable using the exemplary sensors and methods herein disclosed.

FIGS. 21A and 21B are graphical representations showing current verses time of sensors having an enzyme layer comprising a cross-linking agent (i.e., glutaraldehyde; Reference nos. Rcf 11-12, 14-15, 17, 19 and 20; FIG. 21A) and sensors having an enzyme layer absent a cross-linking agent (i.e., no glutaraldehyde added; Reference nos. Rcf 2-3 and 5-10; FIG. 21B) or cross-linking agent reaction products. In both graphs, the x-axis represents time (s=seconds) and the y-axis represents current (A=amps). The sensors were subjected to a PBS solution at pH 7.4 at 37° C., air saturated. The sensors were connected to a potentiostat using a working electrode potential of about 850 mV for 10 minutes before adjusting the voltage to the working potential of about 700 mV vs Ag/AgCl prior to testing. As seen in the graphs, the sensors absent a cross-linking agent showed a current output (FIG. 21B) substantially equivalent to or greater than the control sensors containing a cross-linking agent (FIG. 21A) and therefore are applicable, for example, for very small sensors designed for pediatric and/or neonatal glucose sensing devices that would benefit from the additional current output, such sensors being otherwise compromised by their reduced (e.g., electrode) size. Rapid constant output of the sensors having enzyme membranes absent a cross-linking agent were also substantially equivalent to the control sensors.

It may be seen from the data (FIGS. 14 & 14A) that the break-in time of the exemplary sensors (with the PVP-enzyme composition) had at least equivalent if not superior break-in times to that of the control sensors or comparative sensors (with a separate PVP "electrode domain" or "PBS domain"). As demonstrated, the exemplary sensors had break-in time periods of less than about 30 minutes. Thus, a sensor comprising an electroactive surface, an interference layer and an enzyme layer comprising a hydrophilic polymer-enzyme layer enables rapid and accurate break-in times for a sensor, including not more than about 30 minutes after deployment.

While some prior art interference layers have been known to create altered sensitivity of the sensor to glucose (e.g., variability and/or unreliability of sensors in manufacture), the disclosed glucose sensors constructed with a cellulose acetate butyrate interference layer in contact with at least a portion of an electrochemical surface without an intervening layer, and a hydrophilic enzyme layer in contact with at least a portion of the interference layer without an intervening layer, including embodiments with a PVP as the hydrophilic polymer, provide rapid and accurate glucose sensitivity and consistency.

It has been shown that a sensor having an enzyme layer comprising a hydrophilic polymer-enzyme composition covering at least a portion of the optional interference layer and the electroactive surface as described herein, where the optional interference layer or the hydrophilic polymer-enzyme composition is in contact with the electroactive surface reduced the time required for the detectable output of the sensor to reach a substantially consistent value corresponding to the electrochemically detectable species. It has been shown that the detectable output of the sensor reaches a substantially consistent value corresponding to the electrochemically detectable species substantially immediately in some sensors having a hydrophilic layer covering at least a portion of the optional interference layer, where the interference layer or the hydrophilic polymer-enzyme composition is in contact with the electroactive surface without an intervening layer. It is also believed that the hydrophilic layer may comprise at least one hydrophilic polymer, such as but not limited to PVP, poly-N-vinyl-3-ethyl-2-pyrrolidone, poly-N-vinyl-4,5-dimethyl-2-pyrrolidone, polyacrylamide, poly-N,N-dimethylacrylamide, polyurethane, polyvinyl alcohol, polyethylene glycol, copolymers thereof and mixtures thereof. The preferred hydrophilic polymer is PVP.

It has been shown that a sensor substantially absent an intervening layer between the electroactive surface and an interference layer or a hydrophilic polymer-enzyme composition provide rapid and accurate detectable output of the sensor, which reached a substantially constant value corresponding to the electrochemically detectable species. It has also been shown that a sensor substantially absent a separate intervening layer between the interference layer and the hydrophilic layer reduced the time required for the detectable output of the sensor to reach a substantially constant value corresponding to the electrochemically detectable species. Applicants believe the disclosure and data herein may be extrapolated to in vivo applications without undue experimentation by one of ordinary skill in the art.

Accordingly, sensors and methods have been provided for measuring an analyte in a subject, including a sensor assembly configured for adaption to a continuous glucose monitoring device or a catheter for insertion into a subject's vascular system having electronics unit electrically configurable to the sensor assembly.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification may be to be understood as being modified in all instances by the term "about." Accordingly, unless indicated to the contrary, the numerical parameters set forth herein may be approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials. These descriptions are susceptible to modifications in the methods and materials, as well as alterations in the fabrication methods and equipment. Such modifications will become apparent to those skilled in the art from a consideration of this disclosure or practice of the disclosure. Consequently, it is not intended that this disclosure be limited to the specific embodiments disclosed herein, but that it cover all modifications and alternatives coming within the true scope and spirit of the claims.

What is claimed is:

1. An analyte sensor system comprising:
a glucose sensor comprising:
at least one electrode having an electroactive surface;
optionally an interference layer in contact with at least a portion of the electroactive surface; and
an enzyme layer comprising a hydrophilic polymer-enzyme composition, at least a portion of the enzyme layer covering the electroactive surface, the enzyme layer providing an electrochemically detectable species capable of providing a detectable output; wherein sensor break-in is about 30 minutes or less immediately following deployment;
wherein the hydrophilic polymer of the hydrophilic polymer-enzyme composition comprises a material selected from the group consisting of poly-N-vinylpyrrolidone, poly-N-vinyl-3-ethyl-2-pyrrolidone, poly-N-vinyl-4,5-dimethyl-2-pyrrolidone, polyvinylimidazole, poly-N—N-dimethylacrylamide, polyacrylamide, and copolymers thereof; and
a catheter configured to be inserted into a vascular system of a subject, the catheter having an outer wall and comprising one or more ports formed in the outer wall;
wherein the sensor is positioned at the one or more of the ports.

2. The electrochemical analyte sensor system of claim 1, wherein the hydrophilic polymer-enzyme composition includes reaction products of a cross-linking agent with the hydrophilic polymer-enzyme composition in an amount sufficient to immobilize the enzyme.

3. The electrochemical analyte sensor system of claim 1, wherein said enzyme layer is substantially free of a cross-linking agent or reaction products of a crosslinking agent with the hydrophilic polymer-enzyme composition.

4. The electrochemical analyte sensor system of claim 1, wherein glucose is the analyte capable of providing the electrochemically detectable species and sensor break-in is defined as a detectable output corresponding to within about +/−5 mg/dL of the glucose present at deployment.

5. The electrochemical analyte sensor system as in any one of the preceding claims, characterized by wherein the sensor is substantially absent a separate intervening hydrophilic layer between the electroactive surface and the hydrophilic polymer-enzyme composition.

6. The electrochemical analyte sensor system of claim 1, wherein the interference layer is cellulose acetate butyrate.

7. The electrochemical analyte sensor system of claim 6, characterized by wherein the cellulose acetate butyrate comprises (i) less than about 35% acetyl groups and less than about 25% butyryl groups; (ii) from about 25% to about 34% acetyl groups and from about 15% to about 20% butyryl groups; (iii) about 29.5% acetyl groups and about 17% butyryl groups; (iv) a number average molecular weight of about 65,000 Daltons; or (v) a combination of (iii) and (iv).

8. The electrochemical analyte sensor system of claim 1, wherein the hydrophilic polymer of the hydrophilic-enzyme composition is poly-N-vinylpyrrolidone.

9. The electrochemical analyte sensor system of claim 1, wherein the hydrophilic polymer-enzyme composition comprises poly-N-vinylpyrrolidone, glucose oxidase and at least one protein, or natural or synthetic material, such as a serum albumin.

10. The electrochemical analyte sensor system of claim 1, wherein the sensor is constructed on a flex circuit supporting and electrically coupling to at least one electrode, preferably wherein the flex circuit comprises at least one reference electrode, at least one working electrode, and at least one counter electrode.

11. The electrochemical analyte sensor system of claim 10, wherein the flex circuit is configurable to a catheter for intravenously measuring an analyte concentration in a subject or a continuous blood glucose monitor for continuously measuring the glucose concentration in a subject.

12. The electrochemical analyte sensor system of claim 10, further characterized by: a flex circuit comprising at least one reference electrode and at least one conductive ink working electrode, the at least one conductive ink working electrode having the electroactive surface capable of providing a detectable electrical output upon interaction with an electrochemically detectable species; an optional cellulosic derivative layer; and the enzyme layer covering at least a portion of the electroactive surface of the working electrode; wherein the flex circuit is electrically configurable to a control unit capable of at least receiving the detectable electrical output; wherein sensor break-in is about 30 minutes or less immediately following deployment; optionally wherein the enzyme layer is substantially free of a cross-linking agent or the reaction products of a cross-linking agent and the glucose oxidase.

13. The electrochemical analyte sensor system of claim 10, further characterized by a flex circuit comprising at least one reference electrode and at least one working electrode, the at least one working electrode having an electroactive surface capable of providing a detectable electrical output upon interaction with an electrochemically detectable species; a cellulose acetate butyrate layer; an enzyme layer comprising poly-N-vinylpyrrolidone and glucose oxidase, the enzyme layer in contact with at least a portion of the interference layer, and a membrane comprising vinyl ester monomeric units, the membrane covering the enzyme layer, the interference layer and at least a portion of the electroactive surface of the working electrode; wherein the flex circuit is electrically configurable to a control unit capable of at least receiving the detectable electrical output.

14. The electrochemical analyte sensor system of any one of the claim 1, 6, 10, 12 or 13, further comprising a flux-limiting membrane comprising vinyl acetate monomeric units.

15. The electrochemical analyte sensor system of any one of the claim 1, 6, 10, 12 or 13, further comprising a flux-limiting membrane comprising an ethylene vinyl acetate polymer.

16. The electrochemical analyte sensor system of any one of the claim 1, 6, 10, 12 or 13, further comprising a flux-limiting membrane comprising an ethylene vinyl acetate polymer comprising about 5-40 wt % vinyl acetate.

17. The electrochemical analyte sensor system of any one of the claim 1, 6, 10, 12 or 13, characterized in that the sensor is substantially absent silicone polymers, polyurethane polymers, and their copolymers.

18. An analyte sensor system comprising:
a glucose sensor comprising:

at least one electrode having an electroactive surface;
optionally an interference layer in contact with at least a portion of the electroactive surface; and
an enzyme layer comprising a hydrophilic polymer-enzyme composition, at least a portion of the enzyme layer covering the electroactive surface, the enzyme layer providing an electrochemically detectable species capable of providing a detectable output; wherein sensor break-in is about 30 minutes or less immediately following deployment
wherein the hydrophilic polymer of the hydrophilic polymer-enzyme composition comprises a material selected from the group consisting of poly-N-vinylpyrrolidone, poly-N-vinyl-3-ethyl-2-pyrrolidone, poly-N-vinyl-4,5-dimethyl-2-pyrrolidone, polyvinylimidazole, poly-N—N-dimethylacrylamide, polyacrylamide, and copolymers thereof; and
a catheter configured to be inserted into a vascular system of a subject, the catheter having an outer wall and comprising one or more ports formed in the outer wall;
wherein the sensor is positioned at the one or more of the ports and wherein the sensor is:
substantially absent a separate intervening hydrophilic layer between the electroactive surface and the hydrophilic polymer-enzyme composition;
substantially absent a separate intervening electrolyte layer between the electroactive surface and the interference layer; and
substantially absent a separate intervening electrolyte layer between the interference layer and the enzyme layer;
wherein the sensor is substantially absent silicone polymers, polyurethane polymers, and their copolymers.

* * * * *